(12) United States Patent
Dhawan et al.

(10) Patent No.: US 11,685,709 B2
(45) Date of Patent: Jun. 27, 2023

(54) MULTIPLE CHARGED IONIC COMPOUNDS DERIVED FROM POLYAMINES AND COMPOSITIONS THEREOF AND USE THEREOF AS REVERSE EMULSION BREAKERS IN OIL AND GAS OPERATIONS

(71) Applicant: ECOLAB USA INC., Saint Paul, MN (US)

(72) Inventors: Ashish Dhawan, Saint Paul, MN (US); Keith A. Monk, Saint Paul, MN (US); Carter M. Silvernail, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 199 days.

(21) Appl. No.: 16/554,935

(22) Filed: Aug. 29, 2019

(65) Prior Publication Data
US 2020/0071265 A1    Mar. 5, 2020

Related U.S. Application Data

(60) Provisional application No. 62/724,398, filed on Aug. 29, 2018.

(51) Int. Cl.
*C07C 231/12* (2006.01)
*C07C 227/04* (2006.01)
(Continued)

(52) U.S. Cl.
CPC .......... *C07C 237/10* (2013.01); *C07C 227/04* (2013.01); *C07C 229/16* (2013.01);
(Continued)

(58) Field of Classification Search
None
See application file for complete search history.

(56) References Cited

U.S. PATENT DOCUMENTS

| 2,195,974 A | 4/1940 | Reppe et al. |
| 3,077,487 A | 2/1963 | Ramsey et al. |

(Continued)

FOREIGN PATENT DOCUMENTS

| CN | 1340031 A | 3/2002 |
| CN | 101972612 A | 2/2011 |

(Continued)

OTHER PUBLICATIONS

Zhang et al., "Controllable Self-Assembly of Amphiphilic Dendrimers on a Silica Surface: The Effect of Molecular Topological Structure and Salinity", Journal of Physical Chemistry, vol. 8, pp. 10990-10999, Oct. 5, 2016.

(Continued)

*Primary Examiner* — Amy C Bonaparte
(74) *Attorney, Agent, or Firm* — McKee, Voorhees & Sease, PLC

(57) ABSTRACT

Disclosed herein is a novel class of multiple charged cationic or anionic compounds that are derived from an aza-Michael Addition reaction between a polyamine (Michael donor) and an activated olefin (Michael acceptor), methods of making the same, and use thereof. Also disclosed herein are the methods of using multiple charged cationic or anionic compounds disclosed herein in a reverse emulsion breaker composition to break reverse emulsion commonly found in a produced fluid in oil and gas operations. The disclosed REB methods or compositions are found to be more effective than those methods or compositions including commonly used for oil/solid and water separation.

11 Claims, 2 Drawing Sheets

Polyalkyleneamine

+

Cationic Monomer

Michael Addition →

(I)

(51) Int. Cl.
  *C07C 237/10* (2006.01)
  *C07C 229/16* (2006.01)
  *C09K 8/584* (2006.01)
  *C23F 11/14* (2006.01)
(52) U.S. Cl.
  CPC ............ *C07C 231/12* (2013.01); *C09K 8/584* (2013.01); *C23F 11/145* (2013.01)

(56) References Cited

U.S. PATENT DOCUMENTS

| | | |
|---|---|---|
| 3,793,194 A | 2/1974 | Zecher |
| 3,794,586 A | 2/1974 | Kimura et al. |
| 4,166,894 A * | 9/1979 | Schaper ................ G03G 5/107 528/391 |
| 4,246,030 A | 1/1981 | Lipinski |
| 4,355,071 A | 10/1982 | Chang |
| 4,650,000 A | 3/1987 | Andreasson et al. |
| 4,692,315 A | 9/1987 | Greaves et al. |
| 4,705,665 A | 11/1987 | Malik |
| 4,784,797 A | 11/1988 | Treybig et al. |
| 5,019,343 A | 5/1991 | Hwa et al. |
| 5,053,150 A | 10/1991 | Emert et al. |
| 5,192,798 A | 3/1993 | Aiken et al. |
| 5,614,616 A | 3/1997 | Buysch et al. |
| 5,670,464 A | 9/1997 | Kita et al. |
| 5,738,795 A | 4/1998 | Chen |
| 6,004,466 A | 12/1999 | Derian et al. |
| 6,054,054 A | 4/2000 | Robertson et al. |
| 6,080,323 A | 6/2000 | Yu et al. |
| 6,090,754 A | 7/2000 | Chan et al. |
| 6,238,621 B1 | 5/2001 | Kalota et al. |
| 6,503,880 B1 | 1/2003 | Skold et al. |
| 6,797,785 B1 | 9/2004 | Hund et al. |
| 6,881,710 B1 | 4/2005 | O'Lenick, Jr. et al. |
| 6,984,340 B1 | 1/2006 | Brady et al. |
| 7,052,614 B2 | 5/2006 | Barak |
| 7,084,129 B1 | 8/2006 | Smith et al. |
| 7,345,015 B1 | 3/2008 | Kong et al. |
| 7,507,399 B1 | 3/2009 | O'Lenick, Jr. |
| 7,604,978 B2 | 10/2009 | Eldridge |
| 8,324,264 B1 | 12/2012 | Eldridge et al. |
| 8,933,055 B2 | 1/2015 | Pedersen et al. |
| 9,260,545 B1 | 2/2016 | Squicciarini |
| 9,956,153 B2 | 5/2018 | Emiru et al. |
| 10,850,999 B2 | 12/2020 | DiMascio et al. |
| 10,945,431 B2 | 3/2021 | Karandikar et al. |
| 11,058,111 B2 * | 7/2021 | Dhawan ................ A01N 37/44 |
| 11,084,974 B2 * | 8/2021 | Dhawan ................ C09K 8/588 |
| 11,236,040 B2 * | 2/2022 | Dhawan ................ C07C 237/06 |
| 11,292,734 B2 * | 4/2022 | Dhawan ................ C02F 1/56 |
| 2001/0044393 A1 | 11/2001 | Peterson, Jr. et al. |
| 2002/0155978 A1 | 10/2002 | Man et al. |
| 2003/0121532 A1 | 7/2003 | Coughlin et al. |
| 2005/0215461 A1 | 9/2005 | Gluck et al. |
| 2006/0008496 A1 | 1/2006 | Kulkarni et al. |
| 2006/0289164 A1 | 12/2006 | Smith et al. |
| 2006/0289359 A1 | 12/2006 | Manek et al. |
| 2008/0152567 A1 | 6/2008 | Killough |
| 2009/0236571 A1 | 9/2009 | Cohen |
| 2010/0004316 A1 | 1/2010 | Lu et al. |
| 2010/0029530 A1 | 2/2010 | Whiteley |
| 2010/0305014 A1 | 12/2010 | Miralles et al. |
| 2011/0112007 A1 | 5/2011 | Hodge et al. |
| 2012/0053111 A1 | 3/2012 | Hodge et al. |
| 2012/0070341 A1 | 3/2012 | Eder et al. |
| 2012/0115962 A1 | 5/2012 | Lee et al. |
| 2012/0258157 A1 | 10/2012 | Koltzenburg et al. |
| 2013/0266669 A1 | 10/2013 | Jiang et al. |
| 2014/0124454 A1 | 5/2014 | Nichols et al. |
| 2014/0224733 A1 | 8/2014 | Osness et al. |
| 2015/0290100 A1 | 10/2015 | Eder et al. |
| 2016/0030315 A1 | 2/2016 | Emiru et al. |
| 2016/0130494 A1 | 5/2016 | Zaid et al. |
| 2016/0145610 A1 | 5/2016 | Lu et al. |
| 2016/0262999 A1 | 9/2016 | Pedersen et al. |
| 2016/0264734 A1 | 9/2016 | Boday et al. |
| 2016/0264744 A1 * | 9/2016 | Boday ................ C08G 73/065 |
| 2017/0029691 A1 | 2/2017 | Faust, Jr. et al. |
| 2017/0121560 A1 | 5/2017 | Dockery et al. |
| 2017/0130340 A1 | 5/2017 | Kalakodimi et al. |
| 2017/0233643 A1 | 8/2017 | Agashe et al. |
| 2017/0349543 A1 | 12/2017 | Siegwart et al. |
| 2017/0360040 A1 | 12/2017 | Kost et al. |
| 2018/0007895 A1 | 1/2018 | Karandikar et al. |
| 2018/0066211 A1 | 3/2018 | Pickering et al. |
| 2018/0105629 A1 | 4/2018 | Tada et al. |
| 2018/0118999 A1 | 5/2018 | Hikem et al. |
| 2019/0062187 A1 * | 2/2019 | Dhawan ................ C07F 9/5407 |
| 2019/0223434 A1 | 7/2019 | Balasubramanian et al. |
| 2019/0224627 A1 | 7/2019 | Glanz et al. |
| 2020/0071205 A1 * | 3/2020 | Dhawan ................ C08G 73/02 |
| 2020/0071261 A1 * | 3/2020 | Dhawan ................ C07C 237/10 |
| 2020/0332423 A1 * | 10/2020 | Dhawan ................ C23F 11/173 |
| 2021/0230034 A1 * | 7/2021 | Dhawan ................ C23F 11/141 |

FOREIGN PATENT DOCUMENTS

| | | |
|---|---|---|
| CN | 102675535 A | 9/2012 |
| CN | 103118655 A | 5/2013 |
| CN | 103288672 A | 9/2013 |
| CN | 102675535 B | 11/2013 |
| CN | 104130335 A | 11/2014 |
| CN | 104130351 A | 11/2014 |
| CN | 104744709 A | 7/2015 |
| CN | 105076201 A | 11/2015 |
| CN | 105523956 A | 4/2016 |
| CN | 105884640 A | 8/2016 |
| CN | 106172434 A | 12/2016 |
| CN | 106423269 A | 2/2017 |
| CN | 106423284 A | 2/2017 |
| CN | 106634929 A | 5/2017 |
| CN | 106946743 A | 7/2017 |
| CN | 107440935 A | 12/2017 |
| CN | 108033895 A | 5/2018 |
| CN | 108048249 A | 5/2018 |
| CN | 108938662 A | 12/2018 |
| CN | 111315718 A | 6/2020 |
| EP | 0296441 A2 | 12/1988 |
| GB | 847321 | 9/1960 |
| GB | 1550420 A | 8/1979 |
| JP | 57185322 A | 11/1982 |
| JP | S6259602 * | 3/1987 |
| JP | 6116351 A | 4/1994 |
| JP | 6116898 A | 4/1994 |
| JP | 913066 A | 1/1997 |
| JP | 2001187751 A | 7/2001 |
| JP | 2007054710 A | 3/2007 |
| JP | 2007077082 A | 3/2007 |
| JP | 2007256445 A | 10/2007 |
| JP | 2012136504 A | 7/2012 |
| JP | 2014009177 A | 1/2014 |
| JP | 2014093768 A | 5/2014 |
| JP | 2014221859 A | 11/2014 |
| JP | 2015101552 * | 6/2015 ............ C07C 231/14 |
| JP | 2017525798 A | 9/2017 |
| WO | 2004056843 A2 | 7/2004 |
| WO | WO2009153209 * | 12/2009 |
| WO | 2012083497 A1 | 6/2012 |
| WO | 2013087287 A1 | 6/2013 |
| WO | 2014079621 A1 | 5/2014 |
| WO | 2015084304 A1 | 6/2015 |
| WO | 2016205513 A1 | 12/2016 |
| WO | 2017003639 A2 | 1/2017 |
| WO | 2017201076 A1 | 11/2017 |
| WO | 2018112548 A1 | 6/2018 |
| WO | 2019046409 A1 | 3/2019 |

OTHER PUBLICATIONS

Zhang et al., "Supporting information", Beijing National Laboratory for Molecular Sciences, published with Controllable Self-

(56) References Cited

OTHER PUBLICATIONS

Assembly of Amphiphilic Dendrimers on a Silica Surface, 4 pages, Oct. 5, 2016.
International Preliminary Examining Authority in connection with PCT/US2019/048707 filed Aug. 29, 2019, "The International Preliminary Report on Patentability", 30 pages, dated Jul. 9, 2020.
Fan et al., "Synthesis and Aggregation Behavior of a Hexameric Quaternary Ammonium Surfactant", Langmuir, vol. 27, pp. 10570-10579, Jul. 28, 2011.
Kawakami et al., "Antibacterial Activity of Radial Compounds with Peripheral Quaternary Ammonium Units", Transactions of the Materials Research Society of Japan, vol. 35[4], pp. 885-887, 2010.
Zhang et al., "PAMAM-Based Dendrimers with Different Alkyl Chains Self-Assemble on Silica Surfaces: Controllable Layer Structure and Molecular Aggregation", J. Phys. Chem. B, vol. 122, pp. 6648-6655, Jun. 13, 2018.
Zhou et al., "Cooperative binding and self-assembling behavior of cationic low molecular-weight dendrons with RNA molecules", Organic & Biomolecular Chemistry, vol. 4, pp. 581-585, 2006.
ECOLAB USA Inc., in connection with PCT/US2019/048707 filed Aug. 29, 2019, "The International Search Report and the Written Opinion of the International Searching Authority, or the Declaration", 24 pages, dated Jan. 10, 2020.
Labade et al., "Cesium fluoride catalyzed Aza-Michael addition reaction in aqueous media", Monatsh Chem., vol. 142, pp. 1055-1059, Jul. 19, 2011.
Zielinski et al., "Synthesis of new quaternary ammonium salts for organophilization of fillers for polymeric nanocomposites", www.miesiecznikchemik.pl, 2007.
Somerscales, Euan F.C., "Fundamentals of Corrosion Fouling", Experimental Thermal and Fluid Science, vol. 14, pp. 335-355, 1997.
Zielinksi, Wojciech et al., "TI—Synthesis of new quaternary ammonium salts for organophilization of fillers for polymeric nanocomposites", D1: Database Chemical Abstracts [Online] chemical abstracts; XP55789968, Database accession No. 2007:1236240 Jan. 1, 2007.
"Azamethonium", http://pubchem.ncbi.nlm.nih.gov/compound/9383, last modified Oct. 6, 2018 and accessed by Applicant Oct. 11, 2018.
Bi et al., "Dendrimer-Based Demulsifiers for Polymer Flooding Oil-in-Water Emulsions", Energy Fuels, vol. 31. No. 5, pp. 5395-5401, Apr. 20, 2017, abstract only.
Brycki et al., "The biodegradation of monomeric and dimeric alkylammonium surfactants", Journal of Hazardous Vaterials, vol. 280, pp. 797-815, Sep. 15, 2014, abstract only.
Gan et al., "Sugar-Based Ester Quaternary Ammonium Compounds and Their Surfactant Properties", Journal of Surfactants and Detergents, vol. 17, Issue 3, pp. 465-470, Jan. 18, 2014, abstract only.
Kramer et al., "Dendritic polyamines: simple access to new materials with defined treelike structures for application in nonviral gene delivery", Chembiochem, vol. 5(8), pp. 1081-1087, Aug. 6, 2004, abstract only.
Miller et al., "Non-viral CRISPR/Cas gene editing in vitro and in vivo enabled by synthetic nanoparticle co-delivery of Cas9 mRNA and sgRNA", Angew Chem Int Ed Engl., vol. 56(4), pp. 1059-1063, Jan. 19, 2017.
Negm et al., "Synthesis, Characterization and Biological Activity of Sugar-Based Gemini Cationic Amphiphiles", Journal of Surfactants and Detergents, vol. 11, Issue 3, pp. 215-221, Jun. 13, 2008, preview from research gate only.

Ning et al., "Synthesis and characterization of a novel non-polyether demulsifier", Chemical Engineer, 3 pages, 2013, abstract only.
Tan et al., "The use of quaternised chitosan-loaded PMMA to inhibit biofilm formation and downregulate the virulence-associated gene expression of antibiotic-resistant *Staphylococcus*", Biomaterials, vol. 33, Issue 2, pp. 365-377, Jan. 2012, abstract only.
Wang et al., "A novel environment-sensitive biodegradable polydisulfide with protonatable pendants for nucleic acid delivery", Journal of Controlled Release, vol. 120, pp. 250-258, May 11, 2007.
Zaky, Mohamad, "Biocidal Activities of Cationic Surface Active Starch and Its Transition Metal Complexes Against Different Bacterial Strains", Journal of Surfactants and Detergents, vol. 13, Issue 3, pp. 255-260, Jul. 2010, abstract only.
Zhi et al., "Self-aggregation and antimicrobial activity of saccharidecationic surfactants", Colloids and Surfaces A: Physicochemical and Engineering Aspects, vol. 456, pp. 231-237, Aug 2014, abstract only.
Bosica et al., "Aza-Michael Mono-addition Using Acidic Alumina under Solventless Conditions", Molecules, vol. 21, 11 pages, Jun. 22, 2016.
Miann et al., "Acetal initiated cyclization of allylsilanes to highly functionalized piperidine derivatives", Tetraedron Letters, vol. 29(26), pp. 3247-3250, 1988.
Registry 790647-93-7, accessed online on Aug. 14, 2021, 1 page, registered Nov. 30, 2004.
Registry 881538-24-5, accessed online on Aug. 14, 2021, 1 page, registered Apr. 21, 2006.
Registry 881538-25-6, accessed online on Aug. 14, 2021, 1 page, registered Apr. 21, 2006.
Registry 881538-26-7, accessed online on Aug. 14, 2021, 1 page, registered Apr. 21, 2006.
Registry 930395-29-2, accessed online on Aug. 14, 2021, 1 page, registered Apr. 17, 2007.
Registry 951236-20-7, accessed online on Aug. 14, 2021, 1 page, registered Oct. 23, 2007.
Registry 951236-22-9, accessed online on Aug. 14, 2021, 1 page, registered Oct. 23, 2007.
Registry 951236-51-4, accessed online on Aug. 14, 2021, 1 page, registered Oct. 23, 2007.
Registry 1025555-14-9, accessed online on Aug. 14, 2021, 1 page, registered Jun. 5, 2008.
Registry 1025555-15-0, accessed online on Aug. 14, 2021, 1 page, registered Jun. 5, 2008.
Registry 1346596-75-5, accessed online on Aug. 14, 2021, 1 page, registered Nov. 30, 2011.
Registry 1346596-76-6, accessed online on Aug. 14, 2021, 1 page, registered Nov. 30, 2011.
Registry 1346596-77-7, accessed online on Aug. 14, 2021, 1 page, registered Nov. 30, 2011.
Registry 1801234-01-4, accessed online on Aug. 14, 2021, 1 page, registered Aug. 3, 2015.
Registry 1801234-02-5, accessed online on Aug. 14, 2021, 1 page, registered Aug. 3, 2015.
Registry 2000293-27-4, accessed online on Aug. 14, 2021, 1 page, registered Sep. 26, 2016.
Registry 2001056-21-7, accessed online on Aug. 14, 2021, 1 page, registered Sep. 27, 2016.
Twyman, Lance J., "Post synthetic modification of the hydrophobic interior of a water-soluble dendrimer", Tetrahedron Letters, vol. 41(35), pp. 6875-6878, 2000.

\* cited by examiner

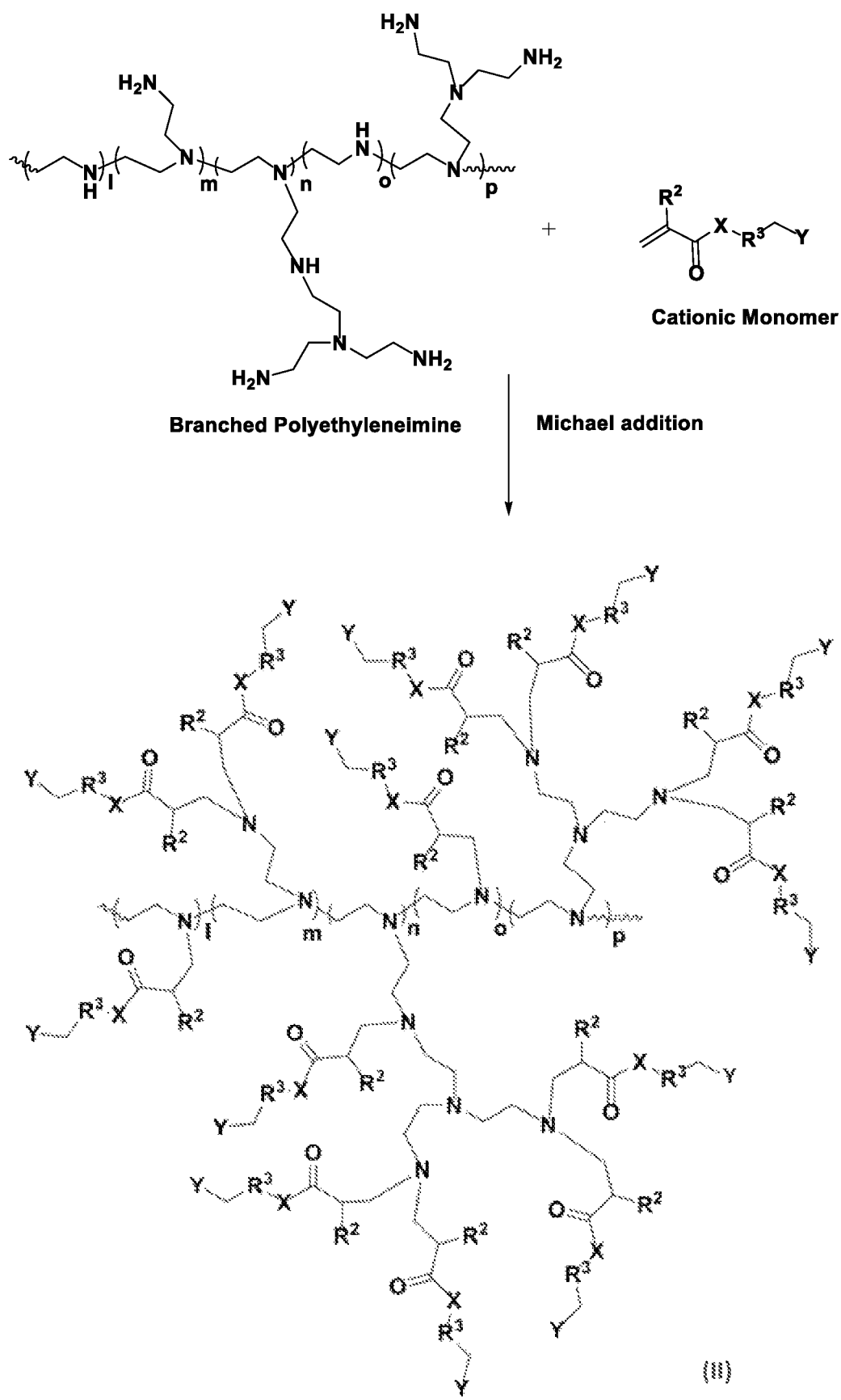

MULTIPLE CHARGED IONIC COMPOUNDS DERIVED FROM POLYAMINES AND COMPOSITIONS THEREOF AND USE THEREOF AS REVERSE EMULSION BREAKERS IN OIL AND GAS OPERATIONS

CROSS-REFERENCE TO RELATED APPLICATIONS

This application claims priority under 35 U.S.C. § 119 to provisional application Ser. No. 62/724,398, filed Aug. 29, 2018, herein incorporated by reference in its entirety.

FIELD OF THE INVENTION

The present invention relates generally to the field of multiple charged cationic or anionic compounds, methods of making the same, and use thereof. The present disclosure also relates generally to the field of using a reverse emulsion breaker composition in oil and gas operations. In particular, the present disclosure relates to a novel class of multiple charged cationic or anionic compounds that are derived from an aza-Michael Addition reaction between a polyamine (Michael donor) and an activated olefin (Michael acceptor), methods of making the same, and use thereof. The disclosed multiple charged cationic or anionic compounds or their salts have at least two or three positive or negative charges within each molecule. The present disclosure also relates to using a reverse emulsion breaker composition comprising one or more multiple charged cationic or anionic compounds disclosed herein for breaking an oil-in-water emulsion or complex emulsion in a produced fluid in oil and gas operations. The disclosed methods, reverse emulsion breaker compositions, multiple charged cationic or anionic compounds herein are effective to separate oil from water than the methods, compositions, or compounds that are currently used in oil and gas operations.

BACKGROUND OF THE INVENTION

Oil-in-water and water-in-oil-in-water emulsions can occur in many industrial systems. For example, a produced fluid containing emulsified oil, e.g., a reverse emulsion or a complex emulsion containing oil-in-water emulsion and dispersed solids, is common in oil and gas operation.

In particular, steam assisted gravity drainage (SAGD) operation injects steam into geological formations to stimulate the production of bitumen or heavy hydrocarbon and generates an oil-in-water and water-in-oil-in-water emulsions. These emulsions contain bitumen and water and need to be broken; the bitumen is sent for upgrading/refining, while the produced water (separated from the emulsion) is treated and reused as feedwater for the steam generators.

From a simple practical point of view, it is highly desirable to separate oil or other hydrocarbon compounds from a produced fluid in oil and gas operations as much as possible before the produced fluid after treatment, a treated produced fluid, is reused for more oil and gas productions or is released into environment.

Indeed, separation of the oil and solids from the water is needed to comply with the oil sales specifications and to provide acceptable specifications before the water can be disposed or re-used.

However, desirable oil/hydrocarbon and water separation for an oil-in-water emulsion or complex emulsion can be difficult by physical processes alone, due to the nature of emulsion. In such circumstances, demulsifying coagulants and flocculants, e.g., a reverse emulsion breaker can be used to break the emulsion and hasten agglomeration of the oil particles. Inorganic coagulants alone or in combination with organic polyelectrolytes have been used in de-emulsification of a produced fluid in oil and gas operations.

Typically, a separation system will have equipment for treating a produced fluid to encourage the further separation of the oil droplets from the water. This equipment includes hydrocyclones, flotation tanks, filtration units, and centrifuges. The performance of these devices can be significantly improved using chemical reverse emulsion breaker agents. The reverse emulsion breakers are referred to interchangeably as deoilers (due to the removal of the oil) or water clarifiers (due to improvement in water quality).

Furthermore, the emulsion droplets that have not been removed by the primary separating system will be significantly stabilized from further coalescence due to two mechanisms. The first is mutual charge repulsion of emulsion droplets. As fluids are processed, the decreasing pressure allows the pH of the water to rise, resulting in the deprotonation of naturally occurring fatty and naphthenic acids present in the crude. These salts provide a negative charge to the emulsion surface and repel other oil droplets that would coalesce upon interaction.

The second is organic and/or inorganic solids adsorbed to the emulsion oil/water interface, effectively sealing the interface from exposure to other emulsion droplets and impeding the coalescence mechanism. If the emulsion droplets are sufficiently small, Brownian motion will keep the emulsion stable indefinitely. For example, in high total dissolved solid (TDS) brines, calcium soaps of fatty/naphthenic acids can form, creating a solid phase at the water interface, making coalescence even slower.

Effective deoiling can be achieved using polyelectrolytes that encourage flocculation of the emulsion droplets into larger collections, which are then more readily acted upon by the physical separation equipment in the water treatment process. The polyelectrolytes neutralize the repulsive charges developed on the emulsion droplets, and if of sufficient size, can also bridge between the droplets, collecting them together into flocculated groups where coalescence may occur due to proximity. Reverse emulsion breakers are designed to function in the high salinity brines common in produced fluids.

For more effective and efficient oil/hydrocarbon separation process, various chemicals as reverse emulsion breakers were invented or investigated. The tried chemicals include various cationic polymer or molecules. However, better reverse emulsion breakers are still needed because the existing ones are unsatisfactory.

Quaternary ammonium compounds have been used for many years as reverse emulsion breaker (REB) agents. Quaternary ammonium compounds belong to an important subcategory of surfactants because they contain unique properties. A main distinction between quaternary ammonium compounds from other surfactants is their unique structure. Quaternary ammonium compounds consist mainly of two moieties, a hydrophobic group, e.g., long alkyl group, and a quaternary ammonium salt group. The unique positive charge of the ammonium plays a key role, e.g., electrostatic interactions, between the surfactant and surface or charge neutralization on surfaces of emulsion droplets. However, the quaternary ammonium compounds used for such purpose are often bis quaternary species or species quaternized with benzyl chloride that are known to be very hazardous. In additional, governmental regulations exist to release any water containing single quaternary compounds into environment.

Therefore, there is a continuing need for different quaternary ammonium compounds that are better and safer reverse emulsion breakers.

Accordingly, it is an objective to develop novel reverse emulsion breaker agents having improved properties having improved oil/hydrocarbon and water separation properties.

It is a further objective of the disclosure to develop a method to make the novel compounds efficiently and effectively.

It is a further objective of the disclosure to use the novel compounds in an article, product, and/or composition.

It is also an objective of the present disclosure to develop new reverse emulsion breakers having improved oil/hydrocarbon and water separation properties.

It is a further objective of the disclosure to develop methods and corresponding reverse emulsion breaker compositions to make the oil/hydrocarbon and water separation in a produced fluid in oil and gas operations more efficient and effective.

These and other objects, advantages and features of the present disclosure will become apparent from the following specification taken in conjunction with the claims set forth herein.

BRIEF SUMMARY OF THE INVENTION

Disclosed herein are novel compounds, methods of making the disclosed compounds, and articles, products, or compositions comprising the disclosed compounds. More particularly, the disclosed herein are the multiple charged cationic or anionic compounds comprising multiple positive or negative charges within single molecules of various molecule sizes and deriving from water soluble polyamine.

Disclosed also herein are methods of using one or more multiple charged cationic or anionic compounds as reverse emulsion breaker in a produced fluid in oil and gas operations. More particularly, the disclosed methods and compositions for breaking oil-in water or complex emulsion in a produced fluid use one or more multiple charged cationic anionic compounds derived from a polyamine.

The exemplary multiple charged cationic compounds disclosed herein show a superior performance than the conventional single quaternary ammonium compounds for breaking reverse emulsion in a produced fluid in oil and gas operations. The exemplary multiple charged cationic compounds disclosed here also show an improved performance when they are used as a coagulant, water clarifier, corrosion inhibitor, clay stabilizer, antimicrobial agent in a water system or in other application. Therefore, the disclosed reverse emulsion breaker compositions or methods have an advantage of not only breaking reverse emulsion but also serving other purposes, leading to overall reduction in chemical uses, cost, and operation complexity.

In one aspect, disclosed herein is a compound derived from an aza-Michael Addition Reaction between a polyamine (Michael donor) and an activated olefin (Michael acceptor) having an ionic group according to one of the following formulas

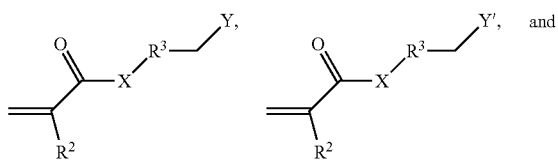

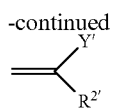

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$, Y' is —COOH, —$SO_3H$, —$PO_3H$, —$OSO_3H$, —$OPO_3H$, or a salt thereof; and $R^4$, $R^5$, and $R^6$ are independently a $C_1$-$C_{10}$ alkyl group; wherein the compound is a multiple charged cationic compound having 2 or more positive charges or multiple charged anionic compound having 2 or more negative charges.

In another aspect, disclosed here is a method of making a compound or its salt, wherein the method comprises contacting a polyamine with an activated olefin (Michael acceptor) having an ionic group according to one of the following formulas

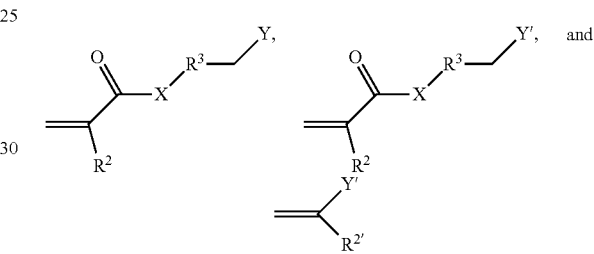

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$, Y' is —COOH, —$SO_3H$, —$PO_3H$, —$OSO_3H$, —$OPO_3H$, or a salt thereof, and $R^4$, $R^5$, and $R^6$ are independently a $C_1$-$C_{10}$ alkyl group; wherein the polyamine and the activated olefin undergo aza-Michael addition reaction; and the compound is a multiple charged cationic compound having 2 or more positive charges or multiple charged anionic compound having 2 or more negative charges.

In yet another aspect, provided herein is an article, product, or composition that comprises one or more compounds disclosed herein.

In yet another aspect, disclosed herein is a composition for resolving a reverse emulsion in a produced fluid from an oil and gas production system, wherein the reverse emulsion breaker composition comprises one or more of the compounds disclosed herein and one or more additional reverse emulsion breaker composition agents. In some embodiments, the reverse emulsion composition disclosed herein breaks oil-in-water emulsion in the produced fluid.

In another aspect, disclosed herein is a method of resolving a reverse emulsion in a produced fluid from an oil and gas production system, wherein the method comprises contacting a produced fluid of an oil and gas production system with a reverse emulsion breaker (REB) composition to generate a treated produced fluid, wherein the reverse emulsion breaker composition comprises one or more of the compounds or their salts and one or more additional reverse emulsion breaker composition agents. In some embodiments, the reverse emulsion composition disclosed herein breaks oil-in-water emulsion in the produced fluid.

The forgoing summary is illustrative only and is not intended to be in any way limiting. In addition to the illustrative aspects, embodiments and features described above, further aspects, embodiments, and features of the present technology will become apparent to those skilled in the art from the following drawings and the detailed description, which shows and describes illustrative embodiments of the present technology. Accordingly, the figures and detailed description are also to be regarded as illustrative in nature and not in any way limiting.

BRIEF DESCRIPTION OF DRAWINGS

FIG. 2 shows an exemplary generic reaction scheme to produce a multiple charged cationic compound by an aza-Michael addition reaction between a branch polyamine and an activated olefin ($\alpha,\beta$-unsaturated carbonyl compound) containing cationic group.

Figure 1:
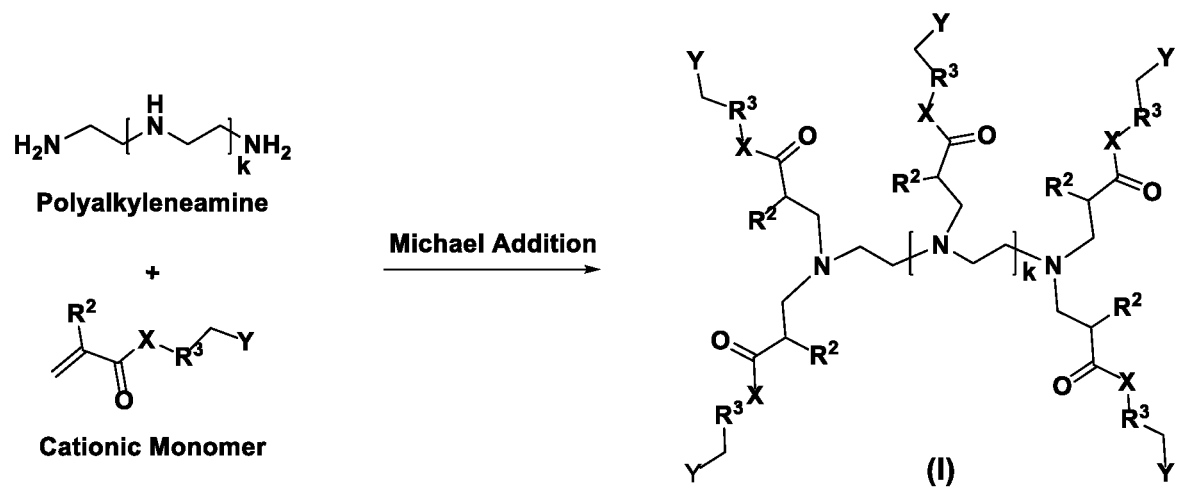
FIG. 1 shows an exemplary generic reaction scheme to produce a multiple charged cationic compound by an aza-Michael addition reaction between a linear polyamine and an activated olefin ($\alpha,\beta$-unsaturated carbonyl compound) containing cationic group.

Various embodiments of the present disclosure will be described in detail with reference to the drawings, wherein like reference numerals represent like parts throughout the several views. Reference to various embodiments does not limit the scope of the disclosure. Figures represented herein are not limitations to the various embodiments according to the disclosure and are presented for exemplary illustration of the disclosure.

DETAILED DESCRIPTION OF THE PREFERRED EMBODIMENT

In the following detailed description, reference may made to the accompanying drawings, schemes, and structures which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

Disclosed herein are methods and compositions for resolving a reverse emulsion in a produced fluid from oil and gas operations. More particularly, one or more multiple charged cationic or anionic compounds are used in the reverse emulsion breaker compositions for resolving reverse emulsions or complex emulsions in produced fluids in oil and gas operations. These multiple charged cationic or anionic compounds are derived from polyamines through an aza-Michael Addition reaction between a polyamine and an activated olefin.

The embodiments of this disclosure are not limited to any specific compositions and methods which can vary and are understood by skilled artisans. It is further to be understood that all terminology used herein is for describing specific embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. The description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation, the preferred materials and methods are described herein. In describing and claiming the embodiments of the present disclosure, the following terminology will be used in accordance with the definitions set out below.

The term "about," as used herein, refers to variation in the numerical quantity that can occur, for example, through typical measuring and liquid handling procedures used for making concentrates or use solutions in the real world; through error in these procedures; through differences in the manufacture, source, or purity of the ingredients used to make the compositions or carry out the methods; and the like. The term "about" also encompasses amounts that differ due to novel equilibrium conditions for a composition resulting from a particular initial mixture. Whether or not modified by the term "about", the claims include equivalents to the quantities.

As used herein, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to carbon(s) or hydrogen(s) atom replaced by one or more bonds, including double or triple bonds, to a heteroatom. Thus, a substituted group is substituted with one or more substituents, unless otherwise specified. A substituted group can be substituted with 1, 2, 3, 4, 5, or 6 substituents.

Substituted ring groups include rings and ring systems in which a bond to a hydrogen atom is replaced with a bond to a carbon atom. Therefore, substituted cycloalkyl, aryl, heterocyclyl, and heteroaryl groups may also be substituted with substituted or unsubstituted alkyl, alkenyl, and alkynyl groups are defined herein.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Alkenyl groups or alkenes are straight chain, branched, or cyclic alkyl groups having two to about 30 carbon atoms, and further including at least one double bond. In some embodiments, an alkenyl group has from 2 to about 30 carbon atoms, or typically, from 2 to 10 carbon atoms. Alkenyl groups may be substituted or unsubstituted. For a double bond in an alkenyl group, the configuration for the double bond can be a trans or cis configuration. Alkenyl groups may be substituted similarly to alkyl groups.

Alkynyl groups are straight chain, branched, or cyclic alkyl groups having two to about 30 carbon atoms, and further including at least one triple bond. In some embodiments, an alkynyl group has from 2 to about 30 carbon atoms, or typically, from 2 to 10 carbon atoms. Alkynyl groups may be substituted or unsubstituted. Alkynyl groups may be substituted similarly to alkyl or alkenyl groups.

As used herein, the terms "alkylene", "cycloalkylene", "alkynylides", and "alkenylene", alone or as part of another substituent, refer to a divalent radical derived from an alkyl, cycloalkyl, or alkenyl group, respectively, as exemplified by —CH$_2$CH$_2$CH$_2$—. For alkylene, cycloalkylene, alkynylene, and alkenylene groups, no orientation of the linking group is implied.

The term "ester" as used herein refers to —R$^3$COOR$^{31}$ group. R$^{30}$ is absent, a substituted or unsubstituted alkylene, cycloalkylene, alkenylene, alkynylene, arylene, aralkylene, heterocyclylalkylene, or heterocyclylene group as defined herein. R$^{31}$ is a substituted or unsubstituted alkyl, cycloalkyl, alkenyl, alkynyl, aryl, aralkyl, heterocyclylalkyl, or heterocyclyl group as defined herein.

The term "amine" (or "amino") as used herein refers to —R$^{32}$NR$^{33}$R$^{34}$ groups. R$^{32}$ is absent, a substituted or unsubstituted alkylene, cycloalkylene, alkenylene, alkynylene, arylene, aralkylene, heterocyclylalkylene, or heterocyclylene group as defined herein. R$^{33}$ and R$^{34}$ are independently hydrogen, or a substituted or unsubstituted alkyl, cycloalkyl, alkenyl, alkynyl, aryl, aralkyl, heterocyclylalkyl, or heterocyclyl group as defined herein.

The term "amine" as used herein also refers to an independent compound. When an amine is a compound, it can be represented by a formula of R$^{32'}$NR$^{33'}$R$^{34'}$ groups, wherein R$^{32'}$, R$^{33'}$, and R$^{34'}$ are independently hydrogen, or a substituted or unsubstituted alkyl, cycloalkyl, alkenyl, alkynyl, aryl, aralkyl, heterocyclylalkyl, or heterocyclyl group as defined herein.

The term "alcohol" as used herein refers to —R$^{35}$OH groups. R$^{35}$ is absent, a substituted or unsubstituted alkylene, cycloalkylene, alkenylene, alkynylene, arylene, aralkylene, heterocyclylalkylene, or heterocyclylene group as defined herein.

The term "carboxylic acid" as used herein refers to —R$^{36}$COOH groups. R$^{36}$ is absent, a substituted or unsubstituted alkylene, cycloalkylene, alkenylene, alkynylene, arylene, aralkylene, heterocyclylalkylene, or heterocyclylene group as defined herein.

The term "ether" as used herein refers to —R$^{37}$OR$^{38}$ groups. R$^{37}$ is absent, a substituted or unsubstituted alkylene, cycloalkylene, alkenylene, alkynylene, arylene, aralkylene, heterocyclylalkylene, or heterocyclylene group as defined herein. R$^{38}$ is a substituted or unsubstituted alkyl, cycloalkyl, alkenyl, alkynyl, aryl, aralkyl, heterocyclylalkyl, or heterocyclyl group as defined herein.

The term "solvent" as used herein refers to any inorganic or organic solvent. Solvents are useful in the disclosed method or composition as reaction solvents or carrier solvents. Suitable solvents include, but are not limited to, oxygenated solvents such as lower alkanols, lower alkyl ethers, glycols, aryl glycol ethers and lower alkyl glycol ethers. Examples of other solvents include, but are not limited to, methanol, ethanol, propanol, isopropanol and butanol, isobutanol, ethylene glycol, diethylene glycol, triethylene glycol, propylene glycol, dipropylene glycol, glycol ethers, mixed ethylene-propylene glycol ethers, ethylene glycol phenyl ether, and propylene glycol phenyl ether. Water is a solvent too. The solvent used herein can be of a single solvent or a mixture of many different solvents.

Glycol ethers include, but are not limited to, diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether, propylene glycol phenyl ether, and the like, or mixtures thereof.

Acids

The compositions disclosed herein may include an acid. However, in some embodiments, the compositions disclosed herein are free of an acid.

Generally, acids, as used in this disclosure, include both organic and inorganic acids. Organic acids include, but not limited to, hydroxyacetic (glycolic) acid, formic acid, acetic acid, propionic acid, butyric acid, valeric acid, caproic acid, gluconic acid, itaconic acid, trichloroacetic acid, urea hydrochloride, and benzoic acid. Organic acids also include dicarboxylic acids such as oxalic acid, malonic acid, succinic acid, glutaric acid, maleic acid, fumaric acid, adipic acid, and terephthalic acid. Combinations of these organic acids can also be used. Inorganic acids include, but are not limited to, mineral acids, such as phosphoric acid, sulfuric acid, sulfamic acid, methylsulfamic acid, hydrochloric acid, hydrobromic acid, hydrofluoric acid, and nitric acid. Inorganic acids can be used alone, in combination with other inorganic acid(s), or in combination with one or more organic acid. Acid generators can be used to form a suitable acid, including for example generators such as potassium fluoride, sodium fluoride, lithium fluoride, ammonium fluoride, ammonium bifluoride, sodium silicofluoride, etc.

Examples of particularly suitable acids in this the methods or compositions disclosed herein include inorganic and organic acids. Exemplary inorganic acids include phosphoric, phosphonic, sulfuric, sulfamic, methylsulfamic, hydrochloric, hydrobromic, hydrofluoric, and nitric. Exemplary organic acids include hydroxyacetic (glycolic), citric, lactic, formic, acetic, propionic, butyric, valeric, caproic, gluconic, itaconic, trichloroacetic, urea hydrochloride, and benzoic. Organic dicarboxylic acids can also be used such as oxalic, maleic, fumaric, adipic, and terephthalic acid.

Percarboxylic Acids and Peroxycarboxylic Acid Compositions

A peroxycarboxylic acid (i.e. peracid) or peroxycarboxylic acid composition can be included in the articles, products, or compositions disclosed herein. As used herein, the term "peracid" may also be referred to as a "percarboxylic acid," "peroxycarboxylic acid" or "peroxyacid." Sulfoperoxycarboxylic acids, sulfonated peracids and sulfonated peroxycarboxylic acids are also included within the terms "peroxycarboxylic acid" and "peracid" as used herein. As one of skill in the art appreciates, a peracid refers to an acid having the hydrogen of the hydroxyl group in carboxylic acid replaced by a hydroxy group. Oxidizing peracids may also be referred to herein as peroxycarboxylic acids.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

A peroxycarboxylic acid composition, as used herein, refers to any composition that comprises one or more peracids, their corresponding acids, and hydrogen peroxide or or other oxidizing agents. A peroxycarboxylic acid composition can also include a stabilizer, fluorescent active tracer or compound, or other ingredients, as one skilled in the other would know.

As used herein, the terms "mixed" or "mixture" when used relating to "percarboxylic acid composition," "percarboxylic acids," "peroxycarboxylic acid composition" or "peroxycarboxylic acids" refer to a composition or mixture including more than one percarboxylic acid or peroxycarboxylic acid. Peracids such as peroxyacetic acid and peroxyoctanoic acid may also be used. Any combination of these acids may also be used.

In some embodiments, however, the articles, products, or compositions disclosed herein are free of a peroxycarboxylic acid or peroxycarboxylic acid composition.

Alkalinity Source or Base

The compositions disclosed herein may include an alkalinity source as a base or alkalinity source. The methods of making disclosed herein may include using an alkalinity source or base as a catalyst. However, in some embodiments, the compositions or methods disclosed herein are free of a base or alkalinity source.

The alkalinity source in turn comprises one or more bases or alkaline compounds. In general, an effective amount of the alkalinity source should be considered as an amount that provides the composition or use solution of the composition having a pH of at least about 8. When the use solution has a pH of between about 8 and about 10, it can be considered mildly alkaline, and when the pH is greater than about 12, the solution can be considered caustic.

The alkalinity source can include an alkali metal carbonate, an alkali metal hydroxide, alkaline metal silicate, alkaline metal metasilicate, or a mixture thereof. Suitable metal carbonates that can be used include, for example, sodium or potassium carbonate, bicarbonate, sesquicarbonate, or a mixture thereof. Suitable alkali metal hydroxides that can be used include, for example, sodium, lithium, or potassium hydroxide. Examples of useful alkaline metal silicates include sodium or potassium silicate (with $M_2O:SiO_2$ ratio of 2.4 to 5:1, M representing an alkali metal) or metasilicate. A metasilicate can be made by mixing a hydroxide and silicate. The alkalinity source may also include a metal borate such as sodium or potassium borate, and the like.

The alkalinity source may also include ethanolamines, urea sulfate, amines, amine salts, and quaternary ammonium. The simplest cationic amines, amine salts and quaternary ammonium compounds can be schematically drawn thus:

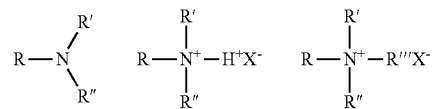

in which, R represents a long alkyl chain, R', R", and R'" may be either long alkyl chains or smaller alkyl or aryl groups or hydrogen and X represents an anion.

In some embodiments, the compositions are free of the alkalinity source or base.

Polyamines

A polyamine can have, but is limited to, a generic formula of $NH_2$—$[R^{10'}]_n$—$NH_2$, $(RNH)_n$—$RNH_2$, $H_2N$—$(RNH)_n$—$RNH_2$, or $H_2N$—$(RN(R'))_n$—$RNH_2$, wherein $R^{10'}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNH_2$, $RNHRNH_2$, or $RN(RNH_2)_2$; and n can be from 2 to 1,000,000. The monomer in a polyamine, e.g., the R or R' group, can be the same or different. In this disclosure, a polyamine refers to both small molecule polyamine when n is from 1 to 9 and polymeric polyamine when n is from 10 to 1,000,000.

Small molecule polyamines include, but are not limited to ethylenediamine, diethylenetriamine, triethylenetetramine, tetraethylenepentamine, pentaethylenehexamine, hexaethyleneheptamine, and tris(2-aminoethyl)amine.

Other possible polyamines include JEFFAMINE® monoamines, diamines, and triamines by Huntsman. These highly versatile products contain primary amino groups attached to the end of a polyether backbone normally based on propylene oxide (PO), ethylene oxide (EO), or a mixture of both oxides. JEFFAMINE® amines include a polyetheramine family consisted of monoamines, diamines and triamines based on the core polyether backbone structure. JEFFAMINE® amines also include high-conversion, and polytetramethylene glycol (PTMEG) based polyetheramines. These JEFFAMINE® amines have an average molecular weight ($M_w$) of from about 130 to about 4,000.

A polyamine used in this disclosure can a polyamine derivative or modified polyamine, in which one or more of the NH protons, but not all, in the polyamine is substituted by an unsubstituted or substituted group. For example, an alkyl polyamine that contains one or more alkyl group connected to the nitrogen atom can be used to produce the multiple charged cationic or anionic compounds disclosed herein. In these PEI derivatives, only some of primary $NH_2$ or secondary NH protons are replaced by other non-proton groups and the remaining $NH_2$ or NH protons can still react with a Michael acceptor, such as an activated olefin containing a hydrophilic (ionic) group, by an aza-Michael Addition reaction.

One class of the polymeric polyamine includes polyethyleneimine (PEI) and its derivatives. Polyethyleneimine (PEI) or polyaziridine is a polymer with a repeating unit of $CH_2CH_2NH$ and has a general formulation of $NH_2(CH_2CH_2NH)_n$—$CH_2CH_2NH_2$, wherein n can be from 2 to $10^5$. The repeating monomer in PEI has a molecular weight of 43.07 and a nitrogen to carbon ratio of 1:2.

PEIs and their derivatives can linear, branched, or dendric. Linear polyethyleneimines contain all secondary amines, in contrast to branched PEIs which contain primary, secondary and tertiary amino groups. Totally branched, dendrimeric forms also exist and contain primary and tertiary amino groups. Drawings for unmodified linear, branched, and dendrimeric PEI are shown below.

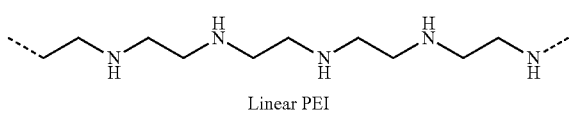

Linear PEI

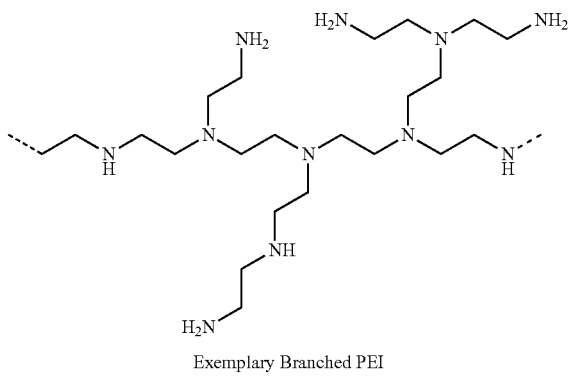

Exemplary Branched PEI

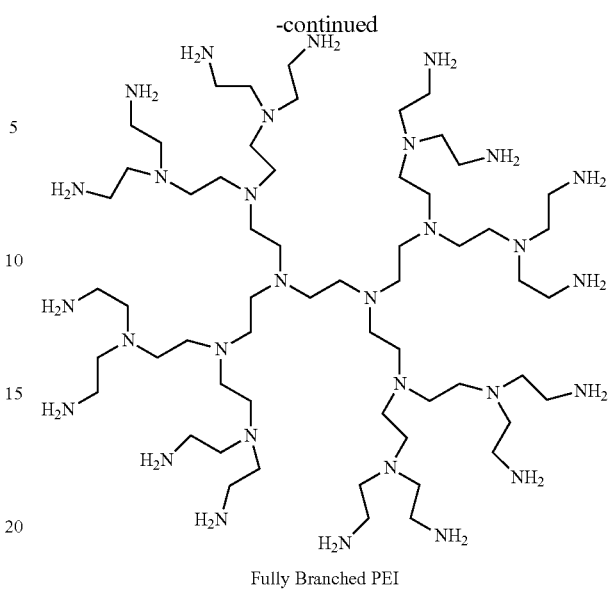

Fully Branched PEI

PEI derivatives are usually obtained by substituting proton(s) on the nitrogen atoms with different group. One such PEI derivative is ethoxylated and propoxylated PEI, wherein the polyethyleneimines are derivatized with ethylene oxide (EO) and/or propylene oxide (PO) side chains. Ethoxylation of PEIs can increase the solubility of PEIs.

PEI is produced on industrial scale. Various commercial polyethyleneimines are available, including for example those sold under the tradename Lupasol® (BASF), including for example Lupasol® FG, Lupasol® G, Lupasol® PR 8515, Lupasol® WF, Lupasol® G 20/35/100, Lupasol® HF, Lupasol® P, Lupasol® PS, Lupasol® PO 100, Lupasol® PN 50/60, and Lupasol® SK. These PEIs have average molecular weights ($M_w$) of about 800, about 1,300, about 2,000, about 5,000, about 25,000, about 1,300/2,000/5,000, about 25,000, about 750,000, about 750,000, about 1,000,000, and about 2,000,000, respectively.

Two common used averages for molecular weight of a polymer are number average molecular weight ($M_n$) and weight average molecular weight ($M_w$). The polydispersity index (D) represents the molecular weight distribution of the polymers. $Mn=(\Sigma n_i M_i)/\Sigma n_i$, $M_w=(\Sigma n_i M_i^2)/\Sigma n_i M_i$, and $D=M_w/M_n$, wherein the index number, i, represents the number of different molecular weights present in the sample and $n_i$ is the total number of moles with the molar mass of $M_i$. For a polymer, $M_n$ and $M_w$ are usually different. For example, a PEI compound can have a $M_n$ of about 10,000 by GPC and $M_w$ of about 25,000 by LS.

Light Scattering (LS) can be used to measure $M_w$ of a polymer sample. Another easy way to measure molecular weight of a sample or product is gel permeation chromatography (GPC). GPC is an analytical technique that separates molecules in polymers by size and provides the molecular weight distribution of a material. GPC is also sometimes known as size exclusion chromatography (SEC). This technique is often used for the analysis of polymers for their both $M_n$ and $M_w$.

These commercially available and exemplary polyethyleneimines are soluble in water and available as anhydrous polyethyleneimines and/or modified polyethyleneimines provided in aqueous solutions or methoxypropanol (as for Lupasol® PO 100).

Suitable polyethyleneimine useful in the present disclosure may contain a mixture of primary, secondary, and tertiary amine substituents or mixture of different average molecular weights. The mixture of primary, secondary, and tertiary amine substituents may be in any ratio, including for example in the ratio of about 1:1:1 to about 1:2:1 with branching every 3 to 3.5 nitrogen atoms along a chain segment. Alternatively, suitable polyethyleneimine compounds may be primarily one of primary, secondary or tertiary amine substituents.

The polyamine that can be used to make the multiple charged cationic or anionic compounds disclosed herein can have a wide range of its average molecular weight. Different multiple charged cationic or anionic compounds with their characteristic average molecular weights can be produced by selecting different starting small molecule polyamines, polymeric PEIs, or mixture thereof. Controlling the size of polyamines or PEI and extent of modification by the activated olefin containing ionic groups, one can produce the multiple charged cationic or anionic compounds with a similar average molecular weight and multiple cationic charges or multiple anionic charges. Because of this character, one can produce and use different multiple charged cationic or anionic compounds for a wider range of applications that are using unmodified polyamine or PEIs.

Specifically, the polyamines that can be used to make the multiple charged cationic or anionic compounds disclosed here have an average molecular weight ($M_w$) of about 60-200, about 100-400, about 100-600, about 600-5,000, about 600-800, about 800-2,000, about 800-5,000, about 100-2,000,000, about 100-25,000, about 600-25,000, about 800-25,000, about 600-750,000, about 800-750,000, about 25,000-750,000, about 750,000-2,000,000, about 100, about 200, about 300, about 400, about 500, about 600, about 700, about 800, about 1,000, about 1,500, about 2,000, about 3,000, about 5,000, about 8,000, about 10,000, about 15,000, about 20,000, about 50,000, about 100,000, about 250,000, about 500,000, about 1,000,000, 2,000,000, or any value there between.

Aza-Michael Addition Reaction Between a Polyamine and Activated Olefin

The multiple charged cationic or anionic compounds disclosed herein are derived from an aza-Michael Addition Reaction between a polyamine and an activated olefin containing a hydrophilic ionic group.

An aliphatic amine group may undergo an aza-Michael Addition reaction when in contact with an unsaturated hydrocarbon moiety (e.g., carbon-carbon double bond) that is in proximity of an electron withdrawing group such as carbonyl, cyano, or nitro group. Specifically, the Michael addition is a reaction between nucleophiles and activated olefin and alkyne functionalities, wherein the nucleophile adds across a carbon-carbon multiple bond that is adjacent to an electron withdrawing and resonance stabilizing activating group, such as a carbonyl group. The Michael addition nucleophile is known as the "Michael donor", the activated electrophilic olefin is known as the "Michael acceptor", and reaction product of the two components is known as the "Michael adduct." Examples of Michael donors include, but are not restricted to, amines, thiols, phosphines, carbanions, and alkoxides. Examples of Michael acceptors include, but are not restricted to, acrylate esters, alkyl methacrylates, acrylonitrile, acrylamides, maleimides, cyanoacrylates and vinyl sulfones, vinyl ketones, nitro ethylenes, α,β-unsaturated aldehydes, vinyl phosphonates, acrylonitrile, vinyl pyridines, azo compounds, beta-keto acetylenes and acetylene esters.

As used herein, an "activated olefin" refers to a substituted alkene in which at least one of the double-bond carbon has a conjugated electron withdrawing group. Examples of activated olefins include, but not limited to, α,β-unsaturated carbonyl compounds (such as $CH_2$=CHCO—NH—$CH_3$, alkyl-CH=CH—CO-alkyl, $CH_2$=$CH_2$C(O)—O—$CH_3$), $CH_2$=CH—COOH, $CH_2$=CH($CH_3$)—COOH, $CH_2$=CH—$SO_3$H, and like.

It was found that the Aza-Michael addition can be used to synthesize the disclosed compounds without having to use a higher temperature greater than 200° C. and high pressure greater than normal atmosphere pressure and with a high yield (greater than 98%) sometimes within about 24 hours.

Aza-Michael addition reaction can be catalyzed by a strong acid or base. In some cases, some ionic liquids can function both as reaction media and catalyst. The preferred catalyst for the Aza-Michael addition reaction to synthesize the disclosed compounds is a base. Exemplary base catalyst can be hydroxide and amines. Because the reaction to synthesize the disclosed compounds uses a polyamine that usually include a polyamine group, the primary amine group itself can function as a catalyst for the reaction. In such embodiments, no additional catalyst is necessary, or an additional catalyst is optional. Other preferred catalysts include amidine and guanidine bases.

The use of solvent and/or diluent for the reaction is optional. When employed, a wide range of non-acidic solvents are suitable, such as, for example, water, ethers (e.g., tetrahydrofuran (THF)), aromatic hydrocarbons (e.g., toluene and xylene), alcohols (e.g., n-butanol), esters (e.g., ethyl 3-ethoxypropionate), and the like. A wide range of solvents can be used for the reaction because the synthesis process is relatively insensitive to solvent. When solvent (or diluent) is employed, loading levels can range from as low as about 10 wt-% up to about 80 wt-% and higher. The solvent loading level can be about 0 wt-%, from about 1 wt-% to about 10 wt-%, from about 10 wt-% to about 20 wt-%, from about 20 wt-% to about 30 wt-%, from about 30 wt-% to about 40 wt-%, from about 40 wt-% to about 50 wt-%, from about 50 wt-% to about 60 wt-%, from about 60 wt-% to about 70 wt-%, from about 70 wt-% to about 80 wt-%, from about 1 wt-% to about 20 wt-%, from about 20 wt-% to about 40 wt-%, from about 40 wt-% to about 60 wt-%, from about 60 wt-% to about 80 wt-%, from about 40 wt-% to about 70 wt-%, at least about 5 wt-%, about 15 wt-%, about 25 wt-%, about 35 wt-%, about 45 wt-%, about 55 wt-%, about 65 wt-%, about 75 wt-%, or any value there between of the final reaction mixture.

Generally, the reaction can be carried out at a temperature over a wide range of temperatures. The reaction temperature can range from about 0° C. to about 150° C., more preferably from about 50° C. to about 80° C. The temperature for contacting the polyamine and activated olefin can be from about 10° C. to about 140° C., about 20° C. to about 130° C., about 30° C. to about 120° C., about 40° C. to about 110° C., about 50° C. to about 100° C., about 60° C. to about 90° C., about 70° C. to about 80° C., about 0° C. to about 20° C., about 20° C. to about 40° C., about 40° C. to about 60° C., about 60° C. to about 80° C., about 80° C. to about 100° C., about 100° C. to about 120° C., about 120° C. to about 150° C., about 5° C., about 25° C., about 45° C., about 65° C., about 85° C., about 105° C., about 125° C., about 145° C., or any value there between. The reaction temperature can be about the same from starting of the reaction to end of the reaction or can be changed from one temperature to another while the reaction is going on.

The reaction time for the synthesis of the compounds disclosed herein can vary widely, depending on such factors as the reaction temperature, the efficacy and amount of the catalyst, the presence or absence of diluent (solvent), and the like. The preferred reaction time can be from about 0.5 hours to about 48 hours, from about 1 hour to about 40 hours, from about 2 hours to about 38 hours, from about 4 hours to about 36 hours, from 6 hours to about 34 hours, from about 8 hours to about 32 hours, from about 10 hours to about 30 hours, from about 12 hours to about 28 hours, from about 14 hours to 26 hours, from about 16 hours to 24 hours, from about 18 hours to 20 hours, from about 1 hour to 8 hours, from 8 hours to 16 hours, from 8 hours to about 24 hours, about 2 hours, about 4 hours, about 6 hours, about 8 hours, about 10 hours, about 14 hours, about 16 hours, about 18 hours, about 24 hours, about 30 hours, about 36 hours, or any values there between.

The reaction for the synthesis of the compounds disclosed herein can go to completion when one mole of the polyamine and two or more moles of the activated olefin are mixed together for a sufficient of time at a temperature described above.

The progression of the reaction can be typically monitored by ESI-MS and/or NMR spectroscopy for consumption of the monomer. The reaction products can be purified or separated by HPLC or other methods known by one skilled in the art. For reactions that proceeded to completion, the formed product can be separated by removal of solvent or by precipitation in a non-polar solvent that was the opposite of the reaction media. For the reactions in water, the formed product is precipitated from the aqueous reaction mixture. Higher pressure can speed-up the reaction. In some embodiments, if the reaction is carried out at a room temperature, the reaction can have a product yield of more than 98%, in some embodiments within about 16 hours.

Other Reverse Emulsion Breaker Composition Agent in a Reverse Emulsion Breaker Composition In addition to the multiple charged cationic or anionic compounds derived from a polyamine as described herein, a reverse emulsion breaker composition in the present disclosure includes one or more additional reverse emulsion breaker composition agents.

The additional reverse emulsion breaker composition agent in the disclosed reverse emulsion breaker compositions can include, but is not limited to, an acid, carrier, dispersant, biocide, inorganic salt, organic salt, emulsifier, additional reverse emulsion breaker, corrosion inhibitor, antioxidant, polymer degradation prevention agent, permeability modifier, foaming agent, antifoaming agent, fracturing proppant, glass particulate, sand, fracture proppant/sand control agent, scavenger for $H_2S$, $CO_2$, and/or $O_2$, gelling agent, lubricant, and friction reducing agent, salt, or mixture thereof.

The additional reverse emulsion breaker composition agent in the disclosed REB compositions can also include, but not be limited to, an organic sulfur compound, de-emulsifier, asphaltene inhibitor, paraffin inhibitor, scale inhibitor, water clarifier, emulsion breaker, reverse emulsion breaker, gas hydrate inhibitor, a pH modifier, a surfactant, or a combination thereof.

Furthermore, the additional reverse emulsion breaker composition agent can be a sequestrant, solubilizer, lubricant, buffer, cleaning agent, rinse aid, preservative, binder, thickener or other viscosity modifier, processing aid, carrier, water-conditioning agent, or foam generator, threshold agent or system, aesthetic enhancing agent (e.g., dye, odorant, perfume), or other additive suitable for formulation with a reverse emulsion breaker, or mixtures thereof.

The additional reverse emulsion breaker composition agent in a REB composition will vary according to the particular reverse emulsion breaker composition being manufactured and its intend use as one skilled in the art will appreciate.

Alternatively, the reverse emulsion breaker composition does not contain or is free of one or more of the additional reverse emulsion breaker composition agents.

When one or more additional reverse emulsion breaker composition agents are used for resolving reverse emulsion or complex emulsion, they can be formulated together with the multiple charged cationic or anionic compounds derived from a polyamine as described here in the same reverse emulsion breaker composition. Alternatively, some or all the additional reverse emulsion breaker composition agents can be formulated into one or more different formulations and be supplied to the produced fluid. In other words, the additional reverse emulsion breaker composition agents can be provided into a produced fluid independently, simultaneously, or sequentially.

Biocide and Carrier

In some embodiments, the reverse emulsion breaker compositions disclosed herein further include a biocide. In some other embodiments, the disclosed reverse emulsion breaker compositions herein further include a carrier. In some other embodiments, the disclosed reverse emulsion breaker compositions herein further include a biocide and carrier. In some embodiments, the disclosed methods or reverse emulsion breaker compositions herein may consist of one or more multiple charged cationic or anionic compounds disclosed herein and carrier. In some embodiments, the reverse emulsion breaker compositions disclosed herein consist of one or more multiple charged cationic or anionic compounds disclosed herein, a carrier, and a biocide.

Biocides suitable for use may be oxidizing or non-oxidizing biocides. Oxidizing biocides include, but are not limited to, bleach, chlorine, bromine, chlorine dioxide, peroxycarboxylic acid, peroxycarboxylic acid composition, and materials capable of releasing chlorine, bromine, or peroxide. Non-oxidizing biocides include, but are not limited to, glutaraldehyde, isothiazolin, 2,2-dibromo-3-nitrilopropionamide, 2-bromo-2-nitropropane-1,3 diol, 1-bromo-1-(bromomethyl)-1,3-propanedicarbonitrile, tetrachloroisophthalonitrile, alkyldimethylbenzylammonium chloride, dimethyl dialkyl ammonium chloride, didecyl dimethyl ammonium chloride, poly(oxyethylene(dimethyliminio)ethylene(dimethyliminio)ethylene dichloride, methylene bisthiocyanate, 2-decylthioethanamine, tetrakishydroxymethyl phosphonium sulfate, dithiocarbamate, cyanodithioimidocarbonate, 2-methyl-5-nitroimidazole-1-ethanol, 2-(2-bromo-2-nitroethenyl)furan, beta-bromo-beta-nitrostyrene, beta-nitrostyrene, beta-nitrovinyl furan, 2-bromo-2-bromomethyl glutaronitrile, bis(trichloromethyl) sulfone, S-(2-hydroxypropyl)thiomethanesulfonate, tetrahydro-3,5-dimethyl-2H-1,3,5-hydrazine-2-thione, 2-(thiocyanomethylthio)benzothiazole, 2-bromo-4'-hydroxyacetophenone, 1,4-bis (bromoacetoxy)-2-butene, bis(tributyltin)oxide, 2-(tert-butylamino)-4-chloro-6-(ethylamino)-s-triazine, dodecylguanidine acetate, dodecylguanidine hydrochloride, coco alkyldimethylamine oxide, n-coco alkyltrimethylenediamine, tetra-alkyl phosphonium chloride, 7-oxabicyclo [2.2.1]heptane-2,3-dicarboxylic acid, 4,5-dichloro-2-n-octyl-4-isothiazoline-3-one, 5-chloro-2-methyl-4-isothiazolin-3-one and 2-methyl-4-isothiazolin-3-one.

Suitable non-oxidizing biocides also include, for example, aldehydes (e.g., formaldehyde, glutaraldehyde, and acrolein), amine-type compounds (e.g., quaternary amine compounds and cocodiamine), halogenated compounds (e.g., 2-bromo-2-nitropropane-3-diol (Bronopol) and 2-2-dibromo-3-nitrilopropionamide (DBNPA)), sulfur compounds (e.g., isothiazolone, carbamates, and metronidazole), and quaternary phosphonium salts (e.g., tetrakis(hydroxymethyl)-phosphonium sulfate (THPS)).

Suitable oxidizing biocides include, for example, sodium hypochlorite, trichloroisocyanuric acids, dichloroisocyanuric acid, calcium hypochlorite, lithium hypochlorite, chlorinated hydantoins, stabilized sodium hypobromite, activated sodium bromide, brominated hydantoins, chlorine dioxide, ozone, peroxycarboxylic acid, peroxycarboxylic acid composition, and peroxides.

The composition can comprise from about 0.1 wt-% to about 10 wt-%, from about 0.5 wt-% to about 5 wt-%, or from about 0.5 wt-% to about 4 wt-% of a biocide, based on total weight of the composition.

A carrier in the disclosed reverse emulsion breaker composition can be water, an organic solvent, or a combination of water and an organic solvent. The organic solvent can be an alcohol, a hydrocarbon, a ketone, an ether, an alkylene glycol, a glycol ether, an amide, a nitrile, a sulfoxide, an ester, or a combination thereof. Examples of suitable organic solvents include, but are not limited to, methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, or a combination thereof.

The composition can comprise from about 1 wt-% to about 80 wt-%, from about 5 wt-% to about 50 wt-%, from about 5 wt-% to about 45 wt-%, from about 5 wt-% to about 30 wt-%, from about 5 wt-% to about 25 wt-%, from about 5 wt-% to about 20 wt-%, from about 5 wt-% to about 15 wt-%, from about 5 wt-% to about 10 wt-%, from about 10 wt-% to about 35 wt-%, from about 10 wt-% to about 25 wt-%, or from about 10 wt-% to about 35 wt-% of the one or more carriers, based on total weight of the composition.

Corrosion Inhibitor

In some embodiments, the reverse emulsion breaker compositions disclosed herein further include a corrosion inhibitor. In some other embodiments, the disclosed reverse emulsion breaker compositions herein further include a corrosion inhibitor and carrier. In some other embodiments, the disclosed reverse emulsion breaker compositions herein further include a corrosion inhibitor, biocide, and carrier. In some embodiments, the disclosed reverse emulsion breaker compositions herein may consist of one or more multiple charged cationic or anionic compounds disclosed herein, one or more corrosion inhibitors and carrier. In some embodiments, the reverse emulsion breaker compositions disclosed herein consist of one or more multiple charged cationic or anionic compounds disclosed herein, a carrier, corrosion inhibitor, and a biocide.

The reverse emulsion breaker composition can comprise from about 0.1 wt-% to about 20 wt-%, from about 0.1 wt-% to about 10 wt-%, or from 0.1 to about 5 wt-% of one or more corrosion inhibitors, based on total weight of the composition. A composition of the disclosure can comprise from about 0 wt-% to about 10 wt-% of the one or more corrosion inhibitors, based on total weight of the composition. The composition can comprise about 1.0 wt-%, about 1.5 wt-%, about 2.0 wt-%, about 2.5 wt-%, about 3.0 wt-%, about 3.5 wt-%, about 4.0 wt-%, about 4.5 wt-%, about 5.0 wt-%, about 5.5 wt-%, about 6.0 wt-%, about 6.5 wt-%, about 7.0 wt-%, about 7.5 wt-%, about 8.0 wt-%, about 8.5 wt-%, about 9.0 wt-%, about 9.5 wt-%, about 10.0 wt-%, about 10.5 wt-%, about 11.0 wt-%, about 11.5 wt-%, about 12.0 wt-%, about 12.5 wt-%, about 13.0 wt-%, about 13.5 wt-%, about 14.0 wt-%, about 14.5 wt-%, or about 15.0 wt-% of the one or more corrosion inhibitors, based on total weight of the composition. Each produced fluid can have its own requirements for using a corrosion inhibitor, and the weight percent of one or more corrosion inhibitors in the composition can vary with the produced fluid in which it is used.

A corrosion inhibitor is needed to reduce corrosion of metals that make contact with the produced fluid. Corrosion inhibitors for multi-metal protection are typically triazoles, such as, but not limited to, benzotriazole, halogenated triazoles, and nitro-substituted azoles.

The one or more corrosion inhibitors can be an imidazoline compound, a quaternary ammonium compound, a pyridinium compound, or a combination thereof.

The one or more corrosion inhibitor component can be an imidazoline. The imidazoline can be, for example, imidazoline derived from a diamine, such as ethylene diamine (EDA), diethylene triamine (DETA), triethylene tetraamine (TETA) etc. and a long chain fatty acid such as tall oil fatty acid (TOFA). The imidazoline can be an imidazoline of Formula (TA) or an imidazoline derivative. Representative imidazoline derivatives include an imidazolinium compound of Formula (2A) or a bis-quaternized compound of Formula (3A).

The one or more corrosion inhibitors can include an imidazoline of Formula (TA):

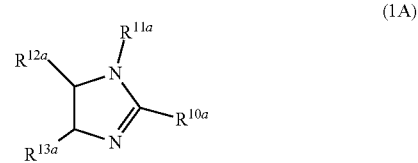

(1A)

wherein $R^{10a}$ is a $C_1$-$C_{20}$ alkyl or a $C_1$-$C_{20}$ alkoxyalkyl group; $R^{11a}$ is hydrogen, $C_1$-$C_6$ alkyl, $C_1$-$C_6$ hydroxyalkyl, or $C_1$-$C_6$ arylalkyl; and $R^{12a}$ and $R^{13a}$ are independently hydrogen or a $C_1$-$C_6$ alkyl group. Preferably, the imidazoline includes an $R^{10a}$ which is the alkyl mixture typical in tall oil fatty acid (TOFA), and $R^{11a}$, $R^{12a}$ and $R^{13a}$ are each hydrogen.

The one or more additional corrosion inhibitors can be an imidazolinium compound of Formula (2A):

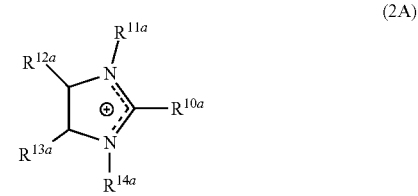

(2A)

wherein $R^{10a}$ is a $C_1$-$C_{20}$ alkyl or a $C_1$-$C_{20}$ alkoxyalkyl group; $R^{11a}$ and $R^{14a}$ are independently hydrogen, $C_1$-$C_6$ alkyl, $C_1$-$C_6$ hydroxyalkyl, or $C_1$-$C_6$ arylalkyl; $R^{12a}$ and $R^{13a}$ are independently hydrogen or a $C_1$-$C_6$ alkyl group; and $X^-$ is a halide (such as chloride, bromide, or iodide), carbonate, sulfonate, phosphate, or the anion of an organic carboxylic acid (such as acetate). Preferably, the imidazolinium compound includes 1-benzyl-1-(2-hydroxyethyl)-2-tall-oil-2-imidazolinium chloride.

The one or more additional corrosion inhibitors can be a bis-quaternized compound having the formula (3A):

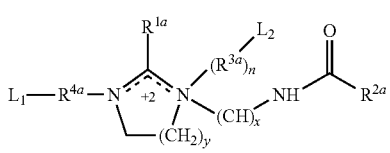

(3A)

wherein $R^{1a}$ and $R^{2a}$ are each independently unsubstituted branched, chain or ring alkyl or alkenyl having from 1 to about 29 carbon atoms; partially or fully oxygenized, sulfurized, and/or phosphorylized branched, chain, or ring alkyl or alkenyl having from 1 to about 29 carbon atoms; or a combination thereof; $R^{3a}$ and $R^{4a}$ are each independently unsubstituted branched, chain or ring alkylene or alkenylene having from 1 to about 29 carbon atoms; partially or fully oxygenized, sulfurized, and/or phosphorylized branched, chain, or ring alkylene or alkenylene having from 1 to about 29 carbon atoms; or a combination thereof; $L_1$ and $L_2$ are each independently absent, H, —COOH, —SO$_3$H, —PO$_3$H, —COOR$^{5a}$, —CONH$_2$, —CONHR$^{5a}$, or —CON(R$^{5a}$)$_2$; R$^{5a}$ is each independently a branched or unbranched alkyl, aryl, alkylaryl, alkylheteroaryl, cycloalkyl, or heteroaryl group having from 1 to about 10 carbon atoms; n is 0 or 1, and when n is 0, $L_2$ is absent or H; x is from 1 to about 10; and y is from 1 to about 5. Preferably, $R^{1a}$ and $R^{2a}$ are each independently $C_6$-$C_{22}$ alkyl, $C_8$-$C_{20}$ alkyl, $C_{12}$-$C_{18}$ alkyl, $C_{16}$-$C_{18}$ alkyl, or a combination thereof; $R^{3a}$ and $R^{4a}$ are $C_1$-$C_{10}$ alkylene, $C_2$-$C_3$ alkylene, $C_2$-$C_6$ alkylene, or $C_2$-$C_3$ alkylene; n is 0 or 1; x is 2; y is 1; $R^3$ and $R^4$ are —C$_2$H$_2$—; $L_1$ is —COOH, —SO$_3$H, or —PO$_3$H; and $L_2$ is absent, H, —COOH, —SO$_3$H, or —PO$_3$H. For example, $R^{1a}$ and $R^{2a}$ can be derived from a mixture of tall oil fatty acids and are predominantly a mixture of $C_{17}H_{33}$ and $C_{17}H_{31}$ or can be $C_{16}$-$C_{18}$ alkyl; $R^{3a}$ and $R^{4a}$ can be $C_2$-$C_3$ alkylene such as —C$_2$H$_2$—; n is 1 and $L_2$ is —COOH or n is 0 and $L_2$ is absent or H; x is 2; y is 1; $R^{3a}$ and $R^{4a}$ are —C$_2$H$_2$—; and $L_1$ is —COOH.

It should be appreciated that the number of carbon atoms specified for each group of formula (3A) refers to the main chain of carbon atoms and does not include carbon atoms that may be contributed by substituents.

The one or more corrosion inhibitors can be a bis-quaternized imidazoline compound having the formula (3A) wherein $R^{1a}$ and $R^{2a}$ are each independently $C_6$-$C_{22}$ alkyl, $C_8$-$C_{20}$ alkyl, $C_{12}$-$C_{18}$ alkyl, or $C_{16}$-$C_{18}$ alkyl or a combination thereof; $R^{4a}$ is $C_1$-$C_{10}$ alkylene, $C_2$-$C_8$ alkylene, $C_2$-$C_6$ alkylene, or $C_2$-$C_3$ alkylene; x is 2; y is 1; n is 0; $L_1$ is-COOH, —SO$_3$H, or —PO$_3$H; and $L_2$ is absent or H. Preferably, a bis-quaternized compound has the formula (3A) wherein $R^{1a}$ and $R^{2a}$ are each independently $C_{16}$-$C_{18}$ alkyl; $R^{4a}$ is —C$_2$H$_2$—; x is 2; y is 1; n is 0; $L_1$ is-COOH, —SO$_3$H, or —PO$_3$H and $L_2$ is absent or H.

The one or more corrosion inhibitors can be a quaternary ammonium compound of Formula (4A):

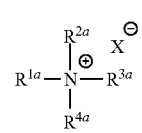

(4A)

wherein $R^{1a}$, $R^{2a}$, and $R^{3a}$ are independently $C_1$ to $C_{20}$ alkyl, $R^{4a}$ is methyl or benzyl, and $X^-$ is a halide or methosulfate.

Suitable alkyl, hydroxyalkyl, alkylaryl, arylalkyl or aryl amine quaternary salts include those alkylaryl, arylalkyl and aryl amine quaternary salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms, and X is Cl, Br or I. For the quaternary salts, R$^{5a}$, R$^{6a}$, R$^{7a}$, and R$^{8a}$ can each be independently alkyl (e.g., $C_1$-$C_{18}$ alkyl), hydroxyalkyl (e.g., $C_1$-$C_{18}$ hydroxyalkyl), and arylalkyl (e.g., benzyl). The mono or polycyclic aromatic amine salt with an alkyl or alkylaryl halide include salts of the formula [N$^+$R$^{5a}$R$^{6a}$R$^{7a}$R$^{8a}$][X$^-$] wherein R$^{5a}$, R$^{6a}$, R$^{7a}$, and R$^{8a}$ contain one to 18 carbon atoms and at least one aryl group, and X is Cl, Br or I.

Suitable quaternary ammonium salts include, but are not limited to, a tetramethyl ammonium salt, a tetraethyl ammonium salt, a tetrapropyl ammonium salt, a tetrabutyl ammonium salt, a tetrahexyl ammonium salt, a tetraoctyl ammonium salt, a benzyltrimethyl ammonium salt, a benzyltriethyl ammonium salt, a phenyltrimethyl ammonium salt, a phenyltriethyl ammonium salt, a cetyl benzyldimethyl ammonium salt, a hexadecyl trimethyl ammonium salt, a dimethyl alkyl benzyl quaternary ammonium salt, a monomethyl dialkyl benzyl quaternary ammonium salt, or a trialkyl benzyl quaternary ammonium salt, wherein the alkyl group has about 6 to about 24 carbon atoms, about 10 and about 18 carbon atoms, or about 12 to about 16 carbon atoms. The quaternary ammonium salt can be a benzyl trialkyl quaternary ammonium salt, a benzyl triethanolamine quaternary ammonium salt, or a benzyl dimethylaminoethanolamine quaternary ammonium salt.

The one or more corrosion inhibitors can be a pyridinium salt such as those represented by Formula (5A):

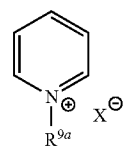

(5A)

wherein $R^{9a}$ is an alkyl group, an aryl group, or an arylalkyl group, wherein said alkyl groups have from 1 to about 18 carbon atoms and $X^-$ is a halide such as chloride, bromide, or iodide. Among these compounds are alkyl pyridinium salts and alkyl pyridinium benzyl quats. Exemplary compounds include methyl pyridinium chloride, ethyl pyridinium chloride, propyl pyridinium chloride, butyl pyridinium chloride, octyl pyridinium chloride, decyl pyridinium chloride, lauryl pyridinium chloride, cetyl pyridinium chloride, benzyl pyridinium chloride and an alkyl benzyl pyridinium chloride, preferably wherein the alkyl is a $C_1$-$C_6$ hydrocarbyl group. Preferably, the pyridinium compound includes benzyl pyridinium chloride.

The one or more additional corrosion inhibitors can be a phosphate ester, monomeric or oligomeric fatty acid, alkoxylated amine, or mixture thereof.

The one or more corrosion inhibitors can be a phosphate ester. Suitable mono-, di- and tri-alkyl as well as alkylaryl phosphate esters and phosphate esters of mono, di, and triethanolamine typically contain between from 1 to about 18 carbon atoms. Preferred mono-, di- and trialkyl phosphate esters, alkylaryl or arylalkyl phosphate esters are those prepared by reacting a $C_3$-$C_{18}$ aliphatic alcohol with phosphorous pentoxide. The phosphate intermediate interchanges its ester groups with triethylphosphate producing a broader distribution of alkyl phosphate esters.

Alternatively, the phosphate ester can be made by admixing with an alkyl diester, a mixture of low molecular weight alkyl alcohols or diols. The low molecular weight alkyl alcohols or diols preferably include $C_6$ to $C_{10}$ alcohols or diols. Further, phosphate esters of polyols and their salts containing one or more 2-hydroxyethyl groups, and hydroxylamine phosphate esters obtained by reacting polyphosphoric acid or phosphorus pentoxide with hydroxylamines such as diethanolamine or triethanolamine are preferred.

The one or more corrosion inhibitors can be a monomeric or oligomeric fatty acid. Preferred monomeric or oligomeric fatty acids are $C_{14}$-$C_{22}$ saturated and unsaturated fatty acids as well as dimer, trimer and oligomer products obtained by polymerizing one or more of such fatty acids.

The one or more corrosion inhibitors can be an alkoxylated amine. The alkoxylated amine can be an ethoxylated alkyl amine. The alkoxylated amine can be ethoxylated tallow amine.

The disclosed multiple charged cationic or anionic compounds were found to be effective as corrosion inhibitors. In some embodiments, the REB compositions disclosed herein are free of a corrosion inhibitor. Because the disclosed multiple charged cationic or anionic compounds can a REB agent and corrosion inhibitor, the disclosed REB compositions have advantages of using less chemicals for oil and gas operations.

Dispersant

In some embodiments, the reverse emulsion breaker compositions disclosed herein can further comprise a dispersant. A dispersant keeps particulate matter present in a produced fluid dispersed, so that it does not agglomerate. The composition can comprise from about 0.1 wt-% to about 10 wt-%, from about 0.5 wt-% to about 5 wt-%, or from about 0.5 wt-% to about 4 wt-% of a dispersant, based on total weight of the composition.

A dispersant may be an acrylic acid polymer, maleic acid polymer, copolymer of acrylic acid with sulfonated monomers, alkyl esters thereof, or combination thereof. These polymers may include terpolymers of acrylic acid, acrylamide and sulfonated monomers. These polymers may also include quad-polymers consisting of acrylic acid and three other monomers.

Suitable dispersants include, but are not limited to, aliphatic phosphonic acids with 2-50 carbons, such as hydroxyethyl diphosphonic acid, and aminoalkyl phosphonic acids, e.g. polyaminomethylene phosphonates with 2-10 N atoms e.g. each bearing at least one methylene phosphonic acid group; examples of the latter are ethylenediamine tetra(methylene phosphonate), diethylenetriamine penta(methylene phosphonate), and the triamine- and tetramine-polymethylene phosphonates with 2-4 methylene groups between each N atom, at least 2 of the numbers of methylene groups in each phosphonate being different. Other suitable dispersion agents include lignin, or derivatives of lignin such as lignosulfonate and naphthalene sulfonic acid and derivatives.

The reverse emulsion breaker composition disclosed herein can further comprise an organic sulfur compound, such as a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof. Preferably, the mercaptoalkyl alcohol comprises 2-mercaptoethanol. Such compounds are used as synergists in the composition. The organic sulfur compound can constitute from about 0.5 wt-% to about 15 wt-% of the composition, based on total weight of the composition, preferably from about 1 wt-% to about 10 wt-% and more preferably from about 1 wt-% to about 5 wt-%. The organic sulfur compound can constitute about 1 wt-%, about 2 wt-%, about 3 wt-%, about 4 wt-%, about 5 wt-%, about 6 wt-%, about 7 wt-%, about 8 wt-%, about 9 wt-%, about 10 wt-%, about 11 wt-%, about 12 wt-%, about 13 wt-%, about 14 wt-%, or about 15 wt-% of the composition.

The reverse emulsion breaker composition can further comprise a de-emulsifier. Preferably, the de-emulsifier comprises an oxyalkylate polymer, such as a polyalkylene glycol. The de-emulsifier can constitute from about 0.1 wt-% to about 10 wt-%, from about 0.5 wt-% to about 5 wt. %, or from about 0.5 wt-% to about 4 wt-% of the composition, based on total weight of the composition. The de-emulsifier can constitute about 0.5 wt-%, about 1 wt-%, about 1.5 wt-%, about 2 wt-%, about 2.5 wt-%, about 3 wt-%, about 3.5 wt-%, about 4 wt-%, about 4.5 wt-%, or about 5 wt-% of the composition.

The reverse emulsion breaker composition can further comprise an asphaltene inhibitor. The composition can comprise from about 0.1 wt-% to about 10 wt-%, from about 0.1 wt-% to about 5 wt-%, or from about 0.5 wt-% to about 4 wt-% of an asphaltene inhibitor, based on total weight of the composition. Suitable asphaltene inhibitors include, but are not limited to, aliphatic sulfonic acids; alkyl aryl sulfonic acids; aryl sulfonates; lignosulfonates; alkylphenol/aldehyde resins and similar sulfonated resins; polyolefin esters; polyolefin imides; polyolefin esters with alkyl, alkylenephenyl or alkylenepyridyl functional groups; polyolefin amides; polyolefin amides with alkyl, alkylenephenyl or alkylenepyridyl functional groups; polyolefin imides with alkyl, alkylenephenyl or alkylenepyridyl functional groups; alkenyl/vinyl pyrrolidone copolymers; graft polymers of polyolefins with maleic anhydride or vinyl imidazole; hyperbranched polyester amides; polyalkoxylated asphaltenes, amphoteric fatty acids, salts of alkyl succinates, sorbitan monooleate, and polyisobutylene succinic anhydride.

The reverse emulsion breaker composition can further comprise a paraffin inhibitor. The composition can comprise from about 0.1 wt-% to about 10 wt-%, from about 0.1 wt-% to about 5 wt-%, or from about 0.5 wt-% to about 4 wt-% of a paraffin inhibitor, based on total weight of the composition. Suitable paraffin inhibitors include, but are not limited to, paraffin crystal modifiers, and dispersant/crystal modifier combinations. Suitable paraffin crystal modifiers include, but are not limited to, alkyl acrylate copolymers, alkyl acrylate vinylpyridine copolymers, ethylene vinyl acetate copolymers, maleic anhydride ester copolymers, branched polyethylenes, naphthalene, anthracene, microcrystalline wax and/or asphaltenes. Suitable paraffin dispersants include, but are not limited to, dodecyl benzene sulfonate, oxyalkylated alkylphenols, and oxyalkylated alkylphenolic resins.

The reverse emulsion breaker composition can further comprise a scale inhibitor. The composition can comprise from about 0.1 wt-% to about 20 wt-%, from about 0.5 wt-% to about 10 wt-%, or from about 1 wt-% to about 5 wt-% of a scale inhibitor, based on total weight of the composition. Suitable scale inhibitors include, but are not limited to, phosphates, phosphate esters, phosphoric acids, phosphonates, phosphonic acids, polyacrylamides, salts of acrylamidomethyl propane sulfonate/acrylic acid copolymer (AMPS/AA), phosphinated maleic copolymer (PHOS/MA), mono-, bis- and oligomeric phosphinosuccinic acid (PSO) derivatives, polycarboxylic acid, hydrophobically modified polycarboxylic acid, and salts of a polymaleic acid/acrylic acid/acrylamidomethyl propane sulfonate terpolymer (PMA/AA/AMPS).

The reverse emulsion breaker composition can further comprise an emulsifier. The composition can comprise from about 0.1 wt-% to about 10 wt-%, from about 0.5 wt-% to about 5 wt-%, or from about 0.5 wt-% to about 4 wt-% of an emulsifier, based on total weight of the composition. Suitable emulsifiers include, but are not limited to, salts of carboxylic acids, products of acylation reactions between carboxylic acids or carboxylic anhydrides and amines, and alkyl, acyl and amide derivatives of saccharides (alkylsaccharide emulsifiers).

The reverse emulsion breaker composition can further comprise a water clarifier. The composition can comprise from about 0.1 wt-% to about 10 wt-%, from about 0.5 wt-% to about 5 wt-%, or from about 0.5 wt-% to about 4 wt-% of a water clarifier, based on total weight of the composition. Suitable water clarifiers include, but are not limited to, inorganic metal salts such as alum, aluminum chloride, and aluminum chlorohydrate, or organic polymers such as acrylic acid-based polymers, acrylamide-based polymers, polymerized amines, alkanolamines, thiocarbamates, and cationic polymers such as acrylamide diallyldimethylammonium chloride (DADMAC) polymer and/or methylacrylamide [3-(Methacryloylamino)propyl]trimethylammonium chloride (MAPTAC) polymer.

The reverse emulsion breaker composition can further comprise an emulsion breaker. The composition can comprise from about 0.1 wt-% to about 10 wt-%, from about 0.5 wt-% to about 5 wt-%, or from about 0.5 wt-% to about 4 wt-% of an emulsion breaker, based on total weight of the composition. Suitable emulsion breakers include, but are not limited to, dodecylbenzylsulfonic acid (DDBSA), the sodium salt of xylenesulfonic acid (NAXSA), epoxylated and propoxylated compounds, anionic, cationic and nonionic surfactants, and resins, such as phenolic and epoxide resins.

In some embodiments, the emulsion breaker (demulsifier) is a nonionic emulsion breaker. The suitable nonionic emulsion breakers include, but are not limited to, poly ethers or oxyalkylates derived from diols, triols, and polyols; polyesters derived from poly ethers and diacids or polyacids such as adipic acid, fumaric acid, maleic anhydride, or acrylic; para-substituted alkyl phenol resin oxyalkylates derived from t-butyl phenol, t-amyl phenol, nonyl phenol, or butyl nonyl phenol; polymerized poly ethers derived from toluene di-isocyanate, diglycidyl ether of bisphenol-A, or acrylic acid; and a combination of resin oxyalkylates and polymerized polyols, such as maleates copolymerized with acrylic acid and then further esterified.

The reverse emulsion breaker composition can further comprise a hydrogen sulfide scavenger. The composition can comprise from about 1 wt-% to about 50 wt-%, from about 1 wt-% to about 40 wt-%, from about 1 wt-% to about 30 wt-%, from about 0.1 wt-% to about 10 wt-%, from about 0.5 wt-% to about 5 wt-%, or from about 0.5 wt-% to about 4 wt-% of a hydrogen sulfide scavenger, based on total weight of the composition. Suitable additional hydrogen sulfide scavengers include, but are not limited to, oxidants (e.g., inorganic peroxides such as sodium peroxide or chlorine dioxide); aldehydes (e.g., of 1-10 carbons such as formaldehyde, glyoxal, glutaraldehyde, acrolein, or methacrolein; triazines (e.g., monoethanolamine triazine, monomethylamine triazine, and triazines from multiple amines or mixtures thereof); condensation products of secondary or tertiary amines and aldehydes, and condensation products of alkyl alcohols and aldehydes.

The reverse emulsion breaker composition can further comprise a gas hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a gas hydrate inhibitor, based on total weight of the composition. Suitable gas hydrate inhibitors include, but are not limited to, thermodynamic hydrate inhibitors (THI), kinetic hydrate inhibitors (KHI), and anti-agglomerates (AA). Suitable thermodynamic hydrate inhibitors include, but are not limited to, sodium chloride, potassium chloride, calcium chloride, magnesium chloride, sodium bromide, formate brines (e.g. potassium formate), polyols (such as glucose, sucrose, fructose, maltose, lactose, gluconate, monoethylene glycol, diethylene glycol, triethylene glycol, mono-propylene glycol, dipropylene glycol, tripropylene glycols, tetrapropylene glycol, monobutylene glycol, dibutylene glycol, tributylene glycol, glycerol, diglycerol, triglycerol, and sugar alcohols (e.g. sorbitol, mannitol)), methanol, propanol, ethanol, glycol ethers (such as diethyleneglycol monomethylether, ethyleneglycol monobutylether), and alkyl or cyclic esters of alcohols (such as ethyl lactate, butyl lactate, methylethyl benzoate).

The reverse emulsion breaker composition can further comprise a kinetic hydrate inhibitor. The composition can comprise from about 0.1 wt-% to about 25 wt-%, from about 0.5 wt-% to about 20 wt-%, from about 1 wt-% to about 10 wt-%, from about 0.1 wt-% to about 10 wt-%, from about 0.5 wt-% to about 5 wt-%, or from about 0.5 wt-% to about 4 wt-% of a kinetic hydrate inhibitor, based on total weight of the composition. Suitable kinetic hydrate inhibitors and anti-agglomerates include, but are not limited to, polymers and copolymers, polysaccharides (such as hydroxyethylcellulose (HEC), carboxymethylcellulose (CMC), starch, starch derivatives, and xanthan), lactams (such as polyvinylcaprolactam, polyvinyl lactam), pyrrolidones (such as polyvinyl pyrrolidone of various molecular weights), surfactants (such as fatty acid salts, ethoxylated alcohols, propoxylated alcohols, sorbitan esters, ethoxylated sorbitan esters, polyglycerol esters of fatty acids, alkyl glucosides, alkyl polyglucosides, alkyl sulfates, alkyl sulfonates, alkyl ester sulfonates, alkyl aromatic sulfonates, alkyl betaine, alkyl amido betaines), hydrocarbon based dispersants (such as lignosulfonates, iminodisuccinates, polyaspartates), amino acids, and proteins.

The reverse emulsion breaker composition can further comprise a pH modifier. The composition can comprise from about 0.1 wt-% to about 20 wt-%, from about 0.5 wt-% to about 10 wt-%, or from about 0.5 wt-% to about 5 wt-% of a pH modifier, based on total weight of the composition. Suitable pH modifiers include, but are not limited to, alkali hydroxides, alkali carbonates, alkali bicarbonates, alkaline earth metal hydroxides, alkaline earth metal carbonates, alkaline earth metal bicarbonates and mixtures or combinations thereof. Exemplary pH modifiers include sodium hydroxide, potassium hydroxide, calcium hydroxide, calcium oxide, sodium carbonate, potassium carbonate, sodium bicarbonate, potassium bicarbonate, magnesium oxide, and magnesium hydroxide.

The reverse emulsion breaker composition can further comprise a surfactant. The composition can comprise from about 0.1 wt-% to about 10 wt-%, from about 0.5 wt-% to about 5 wt-%, or from about 0.5 wt-% to about 4 wt-% of a surfactant, based on total weight of the composition. Suitable surfactants include, but are not limited to, anionic surfactants and nonionic surfactants. Anionic surfactants include alkyl aryl sulfonates, olefin sulfonates, paraffin sulfonates, alcohol sulfates, alcohol ether sulfates, alkyl carboxylates and alkyl ether carboxylates, and alkyl and ethoxylated alkyl phosphate esters, and mono and dialkyl sulfosuccinates and sulfosuccinamates. Nonionic surfactants include alcohol alkoxylates, alkylphenol alkoxylates, block copolymers of ethylene, propylene and butylene oxides, alkyl dimethyl amine oxides, alkyl-bis(2-hydroxyethyl) amine oxides, alkyl amidopropyl dimethyl amine oxides, alkylamidopropyl-bis(2-hydroxyethyl) amine oxides, alkyl polyglucosides, polyalkoxylated glycerides, sorbitan esters and polyalkoxylated sorbitan esters, and alkoyl polyethylene glycol esters and diesters. Also included are betaines and sultanes, amphoteric surfactants such as alkyl amphoacetates and amphodiacetates, alkyl amphopropionates and amphodipropionates, and alkyliminodipropionate.

The reverse emulsion breaker composition can further comprise one or more additional REB composition agents that provide a beneficial property. For example, additional agents can be sequestrants, solubilizers, lubricants, buffers, cleaning agents, rinse aids, preservatives, binders, thickeners or other viscosity modifiers, processing aids, carriers, water-conditioning agents, foam inhibitors or foam generators, threshold agents or systems, aesthetic enhancing agents (e.g., dyes, odorants, perfumes), or other additives suitable for formulation with a corrosion inhibitor composition, and mixtures thereof. Additional agents or additives will vary according to the particular reverse emulsion breaker composition being manufactured and its intend use as one skilled in the art will appreciate.

Alternatively, the reverse emulsion breaker composition does not contain any of the additional agents or additives.

Additionally, the reverse emulsion breaker composition can be formulated into compositions comprising the following components as shown in Table 1. These formulations include the ranges of the components listed and can optionally include additional agents. The values in the Tables below are weight percentages.

TABLE 1

Exemplary Reverse Emulsion Breaker Compositions

| Component | 1 | 2 | 3 | 4 | 5 | 6 | 7 | 8 | 9 | 10 | 11 | 12 |
|---|---|---|---|---|---|---|---|---|---|---|---|---|
| multiple charged cationic or anionic compounds | 0.1-20 | 0.1-20 | 0.1-20 | 0.1-20 | 0.1-20 | 0.1-20 | 10-20 | 10-20 | 10-20 | 10-20 | 10-20 | 0.1-20 |
| diluent | 5-40 | — | 5-50 | — | 5-50 | 5-50 | 5-40 | — | 5-50 | — | — | 10-20 |
| corrosion inhibitor | 0.1-20 | 0.1-20 | — | — | — | — | 0.1-20 | 0.1-20 | — | — | — | 0.1-20 |
| Asphaltene inhibitor | 0.1-5 | 0.1-5 | 0.1-5 | 0.1-5 | — | — | 0.1-5 | 0.1-5 | 0.1-5 | — | — | 0.1-5 |
| Emulsion Breaker | 1-10 | 1-10 | 1-10 | 1-10 | 1-10 | — | 1-10 | 1-10 | 1-10 | 1-10 | — | 1-10 |
| Gas hydrate inhibitor | — | — | — | — | — | — | — | — | — | — | — | 0.1-25 |
| Biocide | 0.5-5 | 0.5-5 | 0.5-5 | 0.5-5 | 0.5-5 | 0.5-5 | 0.5-5 | 0.5-5 | 0.5-5 | 0.5-5 | 0.5-5 | |
| Water | 0.00 | 0-40 | 0-10 | 0-60 | 0-15 | 0-25 | 0.00 | 0-40 | 0-10 | 0-65 | 0-75 | |

| Component | 13 | 14 | 15 | 16 | 17 | 18 | 19 | 20 | 21 | 22 | 23 | 24 |
|---|---|---|---|---|---|---|---|---|---|---|---|---|
| multiple charged cationic or anionic compounds | 0.1-20 | 0.1-20 | 0.1-20 | 0.1-20 | 0.1-20 | 0.1-20 | 10-20 | 10-20 | 10-20 | 10-20 | 10-20 | 10-20 |
| diluent | — | 10-20 | — | 10-35 | 10-35 | — | 10-15 | — | — | 10-35 | 10-35 | — |
| corrosion inhibitor | 0.1-20 | 0.1-20 | 0.1-20 | 0.1-20 | 0.1-20 | 0.1-20 | 0.1-20 | 0.1-20 | 0.1-20 | 0.1-20 | 0.1-20 | 0.1-20 |
| Asphaltene inhibitor | 0.1-5 | — | — | — | — | — | 0.1-5 | — | — | — | — | — |
| Emulsion breaker | 1-10 | 1-10 | — | — | 1-10 | — | 1-10 | 1-10 | — | — | — | 1-10 |
| Gas hydrate inhibitor | 0.1-25 | 0.1-25 | 0.1-25 | — | — | — | 0.1-25 | 0.1-25 | 0.1-25 | — | 0.1-25 | — |
| Biocide | — | — | — | — | — | 0.5-5 | 0.5-5 | 0.5-5 | 0.5-5 | 0.5-5 | — | — |
| Water | 0-20 | 0-5 | 0-35 | 0-25 | 0-15 | 0-55 | 0.00 | 0-20 | 0-30 | 0-20 | 0.00 | 0-50 |

In some embodiments, the reverse emulsion breaker composition or the multiple charged cationic compounds disclosed herein may be added to the produced fluid, so the reverse breaker composition in the treated produced fluid is in an amount ranging from about 1 ppm to about 1000 ppm. In other embodiments, the amount of the reverse emulsion breaker composition or the multiple charged cationic or anionic compounds in the treated produced fluid may range from about 5 ppm to about 200 ppm, from about 10 ppm to about 150 ppm, from about 10 ppm to about 75 ppm, from about 5 ppm to about 50 ppm, from about 5 ppm to about 40 ppm, from about 5 ppm to about 30 ppm, from about 10 ppm to about 60 ppm, from about 10 ppm to about 50 ppm, from about 10 ppm to about 40 ppm, from about 10 ppm to about 75 ppm, from about 20 ppm to about 60 ppm, from about 20 ppm to about 50 ppm, from about 20 ppm to about 40 ppm, or from about 20 ppm to about 30 ppm. In some embodiments, the reverse emulsion breaker composition or the multiple charged cationic or anionic compounds may be added to the produced fluid, so the reverse emulsion breaker composition or the multiple charged cationic or anionic compounds have a concentration of from about 10 ppm to about 200 ppm, from about 10 ppm to about 150 ppm, from about 10 ppm to about 100 ppm, or from about 10 ppm to about 75 ppm in the treated produced fluid.

The reverse emulsion breaker composition or the multiple charged cationic or anionic compounds can be used for breaking reverse emulsion or complex emulsion in a produced fluid in oil and gas applications.

A produced fluid to which the reverse emulsion breaker composition or the multiple charged cationic or anionic compounds can be introduced into can be an aqueous medium. The aqueous medium can comprise water, gas, oil, and optionally liquid hydrocarbon.

A produced fluid to which the reverse emulsion breaker composition or the multiple charged cationic or anionic compounds can be introduced can be a liquid comprising hydrocarbon. The liquid hydrocarbon can be any type of liquid hydrocarbon including, but not limited to, crude oil, heavy oil, processed residual oil, bituminous oil, coker oils, coker gas oils, fluid catalytic cracker feeds, gas oil, naphtha, fluid catalytic cracking slurry, diesel fuel, fuel oil, jet fuel, gasoline, and kerosene. The produced fluid can be a refined hydrocarbon product.

A produced fluid or gas treated with the reverse emulsion breaker composition or the multiple charged cationic or anionic compounds can be at any selected temperature, such as ambient temperature or an elevated temperature. The fluid (e.g., liquid hydrocarbon) or gas can be at a temperature of from about 40° C. to about 250° C. The fluid or gas can be at a temperature of from about −50° C. to about 300° C., from about 0° C. to about 200° C., from about 10° C. to about 100° C., or from about 20° C. to about 90° C. The fluid or gas can be at a temperature of about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or about 40° C. The fluid or gas can be at a temperature of about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or about 100° C.

The reverse emulsion breaker composition or the multiple charged cationic or anionic compounds can be added to a produced fluid at various levels of water cut. For example, the water cut can be from 0% to 100% volume/volume (v/v), from 1% to 80% v/v, or from 1% to 60% v/v. The produced fluid can be an aqueous medium that contains various levels of salinity. The fluid can have a salinity of 0% to 25%, about 1% to 24%, or about 10% to 25% weight/weight (w/w) total dissolved solids (TDS).

The produced fluid or gas in which the reverse emulsion breaker composition or the multiple charged cationic or anionic compounds are introduced can be contained in and/or exposed to many different types of apparatuses. For example, the fluid or gas can be contained in an apparatus that transports fluid or gas from one point to another, such as an oil and/or gas pipeline. The apparatus can be part of an oil and/or gas refinery, such as a pipeline, a separation vessel, a dehydration unit, or a gas line. The fluid can be contained in and/or exposed to an apparatus used in oil extraction and/or production, such as a wellhead. The apparatus can be a cargo vessel, a storage vessel, a holding tank, or a pipeline connecting the tanks, vessels, or processing units.

The reverse emulsion breaker composition or the multiple charged cationic or anionic compounds can be introduced into a produced fluid or gas by any appropriate method for ensuring dispersal through the fluid.

The reverse emulsion breaker composition or the multiple charged cationic or anionic compounds can be added at a point in a flow line upstream from the point at which the produced fluid is processed. The reverse emulsion breaker composition or the multiple charged cationic or anionic compounds can be injected using mechanical equipment such as chemical injection pumps, piping tees, injection fittings, atomizers, quills, and the like.

The reverse emulsion breaker composition or the multiple charged cationic or anionic compounds can be pumped into an oil and/or gas pipeline using an umbilical line. A capillary injection system can be used to deliver the reverse emulsion breaker composition or the multiple charged cationic or anionic compounds to a selected fluid.

The reverse emulsion breaker composition or the multiple charged cationic or anionic compounds can be introduced into a liquid and a mixture of several liquids, a liquid and gas, liquid, solid, and gas. The reverse emulsion breaker composition or the multiple charged cationic or anionic compounds can be injected into a gas stream as an aqueous or non-aqueous solution, mixture, or slurry.

The produced fluid or gas can be passed through an absorption tower comprising the reverse emulsion breaker composition or the multiple charged cationic or anionic compounds.

The reverse emulsion breaker composition or the multiple charged cationic or anionic compounds can be applied to a produced fluid or gas to provide any selected concentration. In practice, the reverse emulsion breaker composition or the multiple charged cationic or anionic compounds are typically added to a flow line to provide an effective treating dose of the reverse emulsion breaker composition or the multiple charged cationic or anionic compounds from about 0.01 to about 5,000 ppm. The reverse emulsion breaker composition or the multiple charged cationic or anionic compounds can be applied to a produced fluid or gas to provide an active concentration of from about 1 parts per million (ppm) to about 1,000,000 ppm, from about 1 parts per million (ppm) to about 100,000 ppm, or from about 10 ppm to about 75,000 ppm. The multiple charged cationic or anionic compounds or their salts/compositions can be applied to a fluid to provide an actives concentration of from about 25 ppm to about 10,000 ppm, from about 25 ppm to about 100 ppm, from about 50 ppm to about 100 ppm, from about 100 ppm to about 10,000 ppm, from about 200 ppm to about 8,000 ppm, or from about 500 ppm to about 6,000 ppm. The actives concentration means the concentration of reverse emulsion breaker composition or the multiple charged cationic or anionic compounds.

The reverse emulsion breaker composition or the multiple charged cationic or anionic compounds can be applied to a produce fluid or gas to provide an active concentration of about 0.1 ppm, about 0.5 ppm, about 1 ppm, about 2 ppm, about 5 ppm, about 10 ppm, about 20 ppm, about 100 ppm, about 200 ppm, about 500 ppm, or about 1,000 ppm in the treated produced fluid. The reverse emulsion breaker composition or the multiple charged cationic or anionic compounds can be applied to a produced fluid to provide an actives concentration of about 0.125 ppm, about 0.25 ppm, about 0.625 ppm, about 1 ppm, about 1.25 ppm, about 2.5 ppm, about 5 ppm, about 10 ppm, or about 20 ppm in the treated produced fluid. Each produced fluid can have its own dose level requirements, and the effective dose level of the reverse emulsion breaker composition or the multiple charged cationic or anionic compounds to sufficiently break reverse emulsion or complex emulsion can vary with the produced fluid in which it is used.

The reverse emulsion breaker composition or the multiple charged cationic or anionic compounds can be applied continuously, in batch, or a combination thereof. The reverse emulsion breaker composition or the multiple charged cationic or anionic compounds dosing can be continuous. The reverse emulsion breaker composition or the multiple charged cationic or anionic compounds dosing can be intermittent (e.g., batch treatment) or can be continuous/maintained and/or intermittent.

Dosage rates for continuous treatments typically range from about 10 to about 500 ppm, or from about 10 ppm to about 200 ppm. Dosage rates for batch treatments typically range from about 10 ppm to about 400,000 ppm, or from about 10 ppm to about 20,000 ppm. The reverse emulsion breaker composition or the multiple charged cationic or anionic compounds can be applied as a pill to a pipeline, providing a high dose (e.g., 20,000 ppm) of the composition.

The flow rate of a flow line in which the reverse emulsion breaker composition or the multiple charged cationic or anionic compounds is used can be between 0.1 and 100 feet per second, or between 0.1 and 50 feet per second. The reverse emulsion breaker composition or the multiple charged cationic or anionic compounds can also be formulated with water to facilitate addition to the flow line.

The reverse emulsion breaker composition or the multiple charged cationic or anionic compounds can be dispensed in any suitable method generally known by one skilled in the art. For example, a spray-type dispenser can be used. A spray-type dispenser functions by impinging a water spray upon an exposed surface of a composition to dissolve a portion of the composition, and then immediately directing the concentrate solution including the composition out of the dispenser to a storage reservoir or directly to a point of use.

The reverse emulsion breaker composition or the multiple charged cationic or anionic compounds can be dispensed by immersing either intermittently or continuously in the water or produced fluid. The reverse emulsion breaker composition or the multiple charged cationic or anionic compounds can then dissolve, for example, at a controlled or predetermined rate. The rate can be effective to maintain a concentration of the dissolved compounds or compositions that are effective for use according to the methods disclosed herein.

The reverse emulsion breaker composition disclosed herein can comprise from about 10 wt-% to about 90 wt-% of the carrier, biocide, corrosion inhibitor, additional REB agent, a combination thereof and from about 10 wt-% to about 90 wt-% of one or more multiple charged cationic or anionic compounds, from about 20 wt-% to about 80 wt-% of the carrier, biocide, corrosion inhibitor, additional REB agent, or combination thereof and from about 20 wt-% to about 80 wt-% of one or more multiple charged cationic or anionic compounds, from about 30 wt-% to about 70 wt-% of the carrier, biocide, corrosion inhibitor, additional REB agent, a combination thereof and from about 30 wt-% to about 70 wt-% of one or more multiple charged cationic or anionic compounds, or from about 40 wt-% to about 60 wt-% of the carrier, biocide, corrosion inhibitor, additional REB agent, a combination thereof and from about 40 wt-% to about 60 wt. % of one or more multiple charged cationic or anionic compounds.

Additionally, when the reverse emulsion breaker is used to break an emulsion for a produced fluid in oil and gas operations, an optional emulsion breaker and the reverse emulsion breaker composition can be added to the produced fluid.

The emulsion breaker can comprise an oxyalkylated phenol-formaldehyde resin, a resin ester, an oxyalkylated polyalkylamine, a polyol, a cross-linked polyol with a di- or multi-functional cross linker, an isocyanate, an acid, or a combination thereof.

The reverse emulsion breaker composition can comprise a mixture of the reverse emulsion breaker and one or more emulsion breakers, depending on the properties of the produced fluid.

In some instances, the emulsion breaker and the reverse emulsion breaker have a synergistic effect for resolving the water-in-oil-in-water emulsion in the produced fluid of an oil production system. The emulsion breaker can have a concentration of from about 100 ppm to about 400 ppm in the produced fluid.

A diluent can be added to the produced fluid and the diluent can be condensate, naphtha, kerosene, light crude oil, or a combination thereof. In some embodiments, a REB composition disclosed herein further comprises a diluent. In some other embodiments, a REB composition disclosed herein further comprises a diluent and one or more emulsion breakers.

Suitable diluents suitable for the REB compositions disclosed herein or suitable to be used together with the REB composition disclosed herein include, but are not limited to, naphtha based diluents and synthetic crude oils (SCO). Naphtha based diluents have typical densities of 650-750 kg/m3 and usually are used for a produced fluid with a high content (for example 70 wt-%) of bitumen. SCOs have typical densities of 650-750 kg/m3 and are used with a produced fluid with a low content (for example 50 wt-%) of bitumen.

In some embodiments, the diluents suitable for the REB compositions disclosed herein is a combination of C4-C5 hydrocarbons with some aromatic hydrocarbons. The aromatic hydrocarbons vary with according to cost and nature of the produced fluid to be treated.

In some embodiments, the diluent is from about 5 wt-% to about 35 wt-% of the REB composition. In some other embodiments, the diluent is from about 5 wt-% to about 15 wt-%, from about 10 wt-% to about 20 wt-%, from about 10 wt-% to about 30 wt-%, from about 15 wt-% to about 20 wt-%, from about 15 wt-% to about 25 wt-%, from about 15 wt-% to about 30 wt-%, from about 15 wt-% to about 35 wt-%, from about 20 wt-% to about 25 wt-%, from about 25 wt-% to about 35 wt-%, from about 30 wt-% to about 35 wt-%, or from about 10 wt-% to about 30 wt-%, of the REB composition.

The reverse emulsion breaker compositions disclosed herein are preferably added to the inlet emulsion to a water and oil separation system. An emulsion breaker, a reverse emulsion breaker, or a combination thereof can be added at an injection point at the inlet pipeline of the produced fluid, before the produced fluid enters one or more separation vessels. When the reverse emulsion breaker is combined with the optional emulsion breaker, they can be injected independently, simultaneously, or sequentially. Further, a diluent can be injected at a different injection point. The separation vessels can be a free water knock out (FWKO) vessel, a heat treater, or a phase separator.

The efficacy of the reverse emulsion breaker composition depends upon a number of factors such as water drop (WD), water quality, interface quality, oil dryness, and the like.

In one aspect, disclosed herein is a compound derived from an aza-Michael Addition Reaction between a polyamine (Michael donor) and an activated olefin (Michael acceptor) having an ionic group according to one of the following formulas

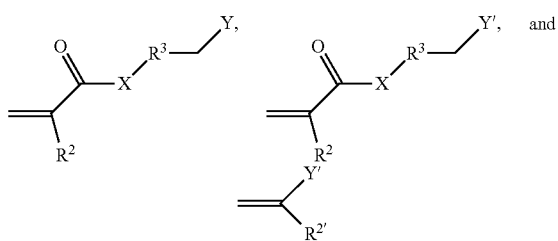

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2COOH$, Y', or —$(CH_2)_m$—Y'; m is an integer of 2 to 4; $R^3$ is absent or an unsubstituted, linear or branched $C_1$-$C_{30}$ alkylene group; Y is —$NR_4R_5R_6^{(+)}$, Y' is —COOH, —$SO_3H$, —$PO_3H$, —$OSO_3H$, —$OPO_3H$, or a salt thereof; and $R^4$, $R^5$, and $R^6$ are independently a $C_1$-$C_{10}$ alkyl group; wherein the compound is a multiple charged cationic or anionic compound having 2 or more positive charges or multiple charged anionic compound having 2 or more negative charges.

In some embodiments, the polyamine is $NH_2$—$[R^{10'}]_n$—$NH_2$, $(RNH)_n$—$RNH_2$, $H_2N$—$(RNH)_n$—$RNH_2$, or $H_2N$—$(RN(R'))_n$—$RNH_2$, wherein $R^{10'}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNH_2$, $RNHRNH_2$, or $RN(RNH_2)_2$; and n can be from 2 to 1,000,000.

The structures of and the reactions leading to the exemplary multiple charged cationic compounds (I) using a linear polyethyleneimine is shown in FIG. 1. The scheme for preparation of exemplary cationic polymer compositions (II) using a branched polyethyleneimine is shown in FIG. 2.

In FIG. 1 and FIG. 2, k, l, m, n, o, or p is an integer of 1-100; X is NH or O; $R^2$ is H, $CH_3$, or an unsubstituted, linear or branched $C_2$-$C_{10}$ alkyl group; $R^3$ is absent or an unsubstituted, linear or branched $C_1$-$C_{30}$ alkylene group; Y is —$NR^4R^5R^{6(+)}$ or a salt thereof; $R^4$, $R^5$, and $R^6$ are independently $C_1$-$C_{10}$ alkyl group or benzyl group.

The structures I and II in FIG. 1 and FIG. 2 are depiction of generalized and exemplary reaction products. In structures I and II, all the secondary and primary amines in the polyethyleneimine react with the activated olefins so that no secondary amines remain. It is possible that in the disclosed multiple charged cationic or anionic compounds, some secondary or primary amine groups do not react completely with the activated olefins and remain as primary or secondary amines in multiple charged cationic or anionic compounds or their salts.

In other words, in some embodiments, the multiple charged cationic or anionic compounds have one of the generic formula of $NA_2$-$[R^{10'}]_n$-$NA_2$, $(RNA)_n$-$RNA_2$, $A_2N$—$(RNA)_n$-$RNA_2$, or $A_2N$—$(RN(R'))_n$—$RNA_2$, wherein $R^{10'}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNA_2$, $RNARNA_2$, or $RN(RNA_2)_2$; n can be from 2 to 1,000,000; A is H or

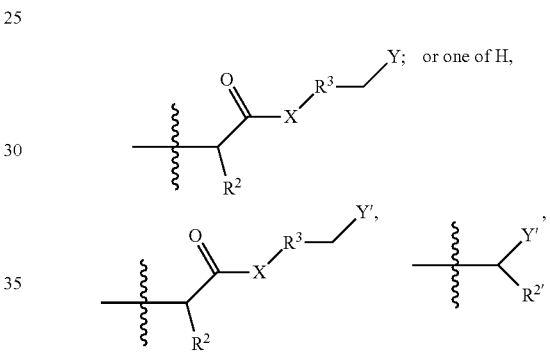

or a combination thereof, each of the compounds contain at least 2 non-proton and cationic or anionic A groups, at least 3 non-proton and cationic or anionic A groups, at least 4 non-proton and cationic or anionic A groups, at least 5 non-proton and cationic or anionic A groups, or more than 6 and cationic or anionic A groups. In some embodiments, A is H or positively charged

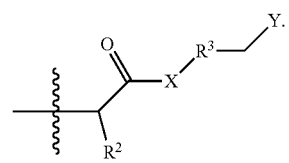

In some other embodiments, A is H or negatively charged

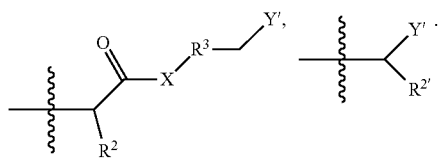

In some embodiments, at least two of the primary $NH_2$ protons are

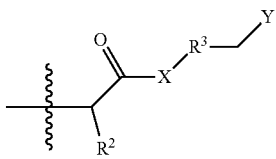

and the rest of primary $NH_2$ protons remains. In some embodiments, at least two of the primary $NH_2$ protons are

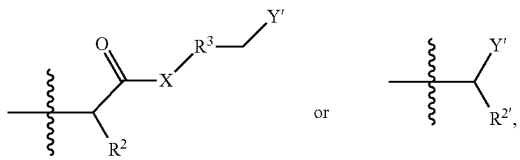

and the rest of primary $NH_2$ protons remains. In some other embodiments, all of the primary $NH_2$ protons are replaced by

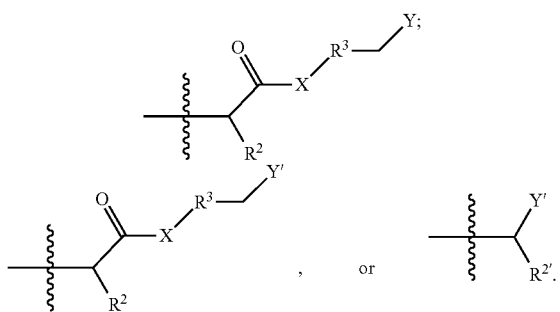

In some embodiments, some of primary $NH_2$ and secondary NH proton are replaced by

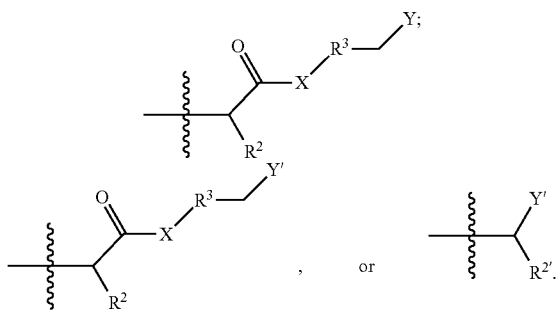

In some embodiments, all of primary $NH_2$ and some of secondary NH proton are replaced by

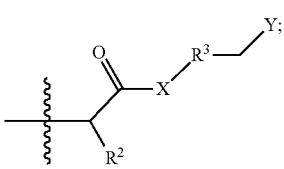

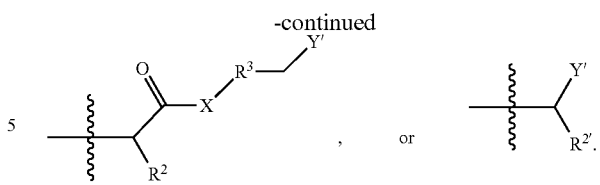

In some embodiments of the disclosed compounds herein, X is NH. In some other embodiments, X is O.

In some embodiments, $R^2$ is H. In some embodiments, $R^2$ is $CH_3$. In yet some other embodiments, $R^2$ is $CH_3CH_3$, $CH_2CH_2CH_3$, or $CH(CH_3)_2$.

In some embodiments, Y is $-NR_4R_5R_6^{(+)}$. In some other embodiments, Y is $-NR_4R_5R_6^{(+)}$, and $R^4$, $R^5$, and $R^6$ are independently $CH_3$. In yet some other embodiments, Y is $-NR_4R_5R_6^{(+)}$, and $R^4$ and $R^5$, independently $CH_3$, and $R^6$ is a $C_2-C_{12}$ aromatic alkyl. In some other embodiments, Y is $-NR_4R_5R_6^{(+)}$, and $R^4$ and $R^5$, independently $CH_3$, and $R^6$ is $-CH_2-C_6H_6$.

In some embodiments, Y is $-NR_4R_5R_6^{(+)}$ and the counter ion for Y any negative charged ion or species. In some other embodiments, the counter ion for Y is chloride, bromide, fluoride, iodide, acetate, aluminate, cyanate, cyanide, dihydrogen phosphate, dihydrogen phosphite, formate, carbonate, hydrogen carbonate, hydrogen oxalate, hydrogen sulfate, hydroxide, nitrate, nitrite, thiocyanate, or a combination thereof.

In some embodiments, Y' is $-COOH$ or salt thereof. In some other embodiments, Y' is $-SO_3H$, $-OSO_3H$ or salt thereof. In yet some other embodiments, Y' is $-OPO_3H$, $-PO_3H$, or salt thereof. In some embodiments, Y' is an acidic species or salt thereof.

In some embodiments, $R^3$ is $CH_2$. In some other embodiments, $R^3$ is $CH_2CH_2$. In other embodiments, $R^3$ is $C(CH_3)_2$. In yet some other embodiments, $R^3$ is an unsubstituted, linear, and saturated $C_1-C_{10}$ alkylene group. In some embodiments, $R^3$ is an unsubstituted, linear, and unsaturated $C_1-C_{10}$ alkylene group.

In some embodiments, $R^3$ is a linear $C_8-C_{18}$ alkyl, alkenyl, or alkynyl group. In some other embodiments, $R^3$ is a branched $C_8-C_{20}$ alkyl, alkenyl, or alkynyl group.

In some embodiments, the polyamine is a linear, branched, or dendrimer polyamine with a general formula of $-[RNH]_n-$, wherein R is $-CH_2CH_2-$, $-CH_2CH_2CH_2-$, $-CH(CH_3)CH_2-$, a linear or branched, unsubstituted or substituted $C_4-C_{10}$ alkylene group, or combination thereof and n is an integer of 3, 4, 5, 6, 7-9, or 10 to 1,000,000.

In some embodiments, the polyamine is a linear, branched, or dendrimer polyamine with a general formula of $(RNH)_n-RNH_2$, wherein R is $-CH_2-$, $-CH_2CH_2-$, $-CH_2CH_2CH_2-$, $-CH(CH_3)CH_2-$, a linear or branched, unsubstituted or substituted $C_4-C_{10}$ alkylene group, or combination thereof and n can be from 2 to 1,000,000. In some embodiments, R is the same in each monomer. In some other embodiments, R can be different from one monomer to another monomer.

In some other embodiments, the polyamine is a linear, branched, or dendrimer polyamine with a general formula of $H_2N-(RNH)_n-RNH_2$, wherein R is $-CH_2-$, $-CH_2CH_2-$, $-CH_2CH_2CH_2-$, $-CH(CH_3)CH_2-$, a linear or branched, unsubstituted or substituted $C_4-C_{10}$ alkylene group, or combination thereof and n can be from 2 to 1,000,000. In some embodiments, R is the same in each monomer. In some other embodiments, R can be different from one monomer to another monomer.

In yet some other embodiments, the polyamine is a linear, branched, or dendrimer polyamine with a general formula of $H_2N-(RN(R'))_n-RNH_2$, wherein R is $-CH_2-$, $-CH_2CH_2-$, $-CH_2CH_2CH_2-$, $-CH(CH_3)CH_2-$, a linear or branched, unsubstituted or substituted $C_4-C_{10}$ alkylene group, or combination thereof; R' is $-CH_2-$, $-CH_2CH_2-$, $-CH_2CH_2CH_2-$, $-CH(CH_3)CH_2-$, a linear or branched, unsubstituted or substituted $C_4-C_{10}$ alkyl group, $RNH_2$, $RNHRNH_2$, or $RN(RNH_2)_2$; and n can be from 2 to 1,000,000. In some embodiments, R or R' is the same in each monomer. In some other embodiments, R or R' can be different from one monomer to another monomer.

In some embodiments, the polyamine is one with a general formula of $NH_2-[R^{10'}]_n-NH_2$, wherein $R^{10'}$ is a linear or branched, unsubstituted or substituted $C_4-C_{10}$ alkylene group, or combination thereof and n is an integer of 3, 4, 5, 6, 7-9, or 10 to 1,000,000. In some other embodiments, $R^{10'}$ can be different from one monomer to another monomer.

In some embodiments, the polyamine is one or more of polyamines under JEFFAMINE® by Huntsman.

In some embodiments, the polyamine comprises an alkyleneamine, the alkyleneamine comprising ethylenediamine, diethylenetriamine, triethylenetetramine, tetraethylenepentamine, pentaethylenehexamine, hexaethyleneheptamine, polyethyleneimine, tris(2-aminoethyl)amine, or a mixture thereof.

In some other embodiments, the polyamine is a mixture of monoamine, diamine, and triamine with a polyether backbone or with a polyether backbone based on propylene oxide (PO), ethylene oxide (EO), or a mixture of both oxides.

In some embodiments, the polyamine is an unmodified polyamine. In some other embodiments, the polyamine is a modified polyamine. As used herein, a "modified polyamine" refers to a polyamine in which one or more NH protons is substituted by a non-proton group, such as an alkyl.

In yet some embodiments, the polyamine is an ethoxylated polyamine, propylated polyamine, polyamine with polyquat, polyamine with polyglycerol, or combination thereof.

In some embodiments, the polyamine is diamine or triamine having an average molecular weight ($M_w$) of from about 130 to about 4,000.

In yet some other embodiments, the polyamine is a linear, branched, or dendrimer polyethyleneimine. In some other embodiments, the polyamine comprises only primary and secondary amine groups. In some embodiments, the polyamine comprises only primary, secondary, and tertiary amine groups. In some other embodiments, the polyamine comprises only primary and tertiary amine groups.

In some embodiments, the polyamine is a single compound. In some other embodiments, the polyamine is a mixture of two or more different polyamines, wherein the different polyamines have different molecular weight, different structure, or both.

In some embodiments, the polyamine has an average molecular weight ($M_w$) of from about 130 to about 2,000,000 Da. In some other embodiments, the polyamine has an average molecular weight ($M_w$) of from about 130 to about 5,000 Da. In yet some other embodiments, the polyamine has an average molecular weight ($M_w$) of from about 130 to about 25,000 Da.

In some embodiments, the polyamine has an average molecular weight ($M_w$) of about 60-200, about 100-400, about 100-600, about 600-5,000, about 600-800, about 800-2,000, about 800-5,000, about 100-2,000,000, about 100-25,000, about 600-25,000, about 800-25,000, about 600-750,000, about 800-750,000, about 25,000-750,000, about 750,000-2,000,000, about 100, about 200, about 300, about 400, about 500, about 600, about 700, about 800, about 1,000, about 1,500, about 2,000, about 3,000, about 5,000, about 8,000, about 10,000, about 15,000, about 20,000, about 50,000, about 100,000, about 250,000, about 500,000, about 1,000,000, about 2,000,000, or any value there between.

In some embodiments, the compound is a mixture derived from a linear polyethyleneimine and (3-acrylamidopropyl) trimethylammonium chloride (APTAC). In some other embodiments, the compound is a mixture derived from a linear polyethyleneimine and [3-(methacryloylamino)propyl]trimethylammonium chloride (MAPTAC).

In some other embodiments, the multiple charged cationic or anionic compound is a mixture derived from a branched polyethyleneimine and (3-acrylamidopropyl)trimethylammonium chloride (APTAC). In some other embodiments, the compound is a mixture derived from a linear polyethyleneimine and [3-(methacryloylamino)propyl]trimethylammonium chloride (MAPTAC).

In some embodiments, the activated olefin is (3-acrylamidopropyl)trimethylammonium chloride (APTAC), [3-(methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), or 2-(methacryloyloxy)-N,N,N-trimethylethan-1-aminium methyl sulfate (DMAEA-MSQ).

In some other embodiments, the activated olefin is (3-acrylamidopropyl)trimethylammonium chloride (APTAC), [3-(methacryloylamino)propyl]trimethylammonium chloride (MAPTAC), or mixture thereof.

In some other embodiments, the activated olefin is 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), or a mixture thereof.

In some embodiments, the activated olefin is acrylic acid, methacrylic acid, itaconic acid, maleic acid, vinylsulfonic acid, vinylphosphonic acid, or mixture thereof.

In some other embodiments, the activated olefin is 2-acrylamido-2-methylpropane sulfonic acid (AMPS), 3-(allyloxy)-2-hydroxypropane-1-sulfonate, or mixture thereof.

In some other embodiments, wherein the activated olefin is vinylsulfonic acid, vinylphosphonic acid, or mixture thereof.

In yet some other embodiments, when the activated olefin contains anionic group that can bear negative charge at an alkaline pH, the counter positive ions for the negative charges include, but are not limited to, alkali metal ions, $Li^+$, $Na^+$, $K^+$, $NH_4^+$, a quaternary ammonium ion, etc.

In some embodiments, the compound is an aza-Michael Addition reaction product of (3-acrylamidopropyl) trimethylammonium chloride (APTAC) and tetraethylenepentamine, E-100 (a mixture of tetraethylenepentamine (TEPA), pentaethylenehexamine (PEHA), and hexaethyleneheptamine (HEHA)), Pentaethylenehexamine (PEHA), or diethylenetriamine (DETA), respectively.

In some embodiments, the compound is an aza-Michael Addition reaction product of (3-acrylamidopropyl) trimethylammonium chloride (APTAC) and a polyethylenimine with an average molecular weight ($M_w$) of about 1,300, a polyethylenimine with an average molecular weight ($M_w$) of about 5,000, a polyethylenimine with an average molecular weight ($M_w$) of about 25,000, or a polyethylenimine with an average molecular weight ($M_w$) of about 750,000, respectively.

In some embodiments, the compound is one or more of

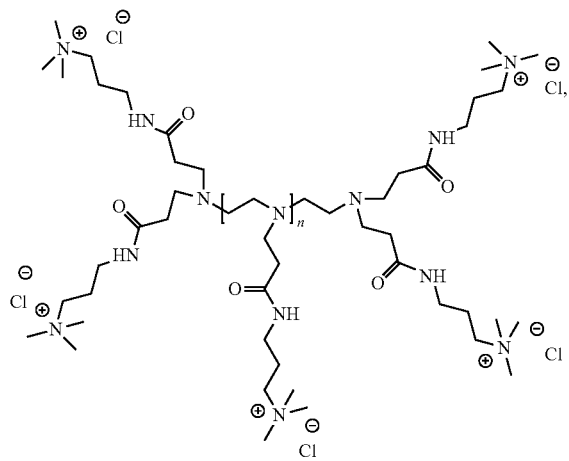

wherein n=0-1000. It should be understood that when n is greater than 2, the compound can be a mixture of more than two cationic compounds, which differ from each other by the exact locations of NH replacements.

In some other embodiments, wherein the compound is

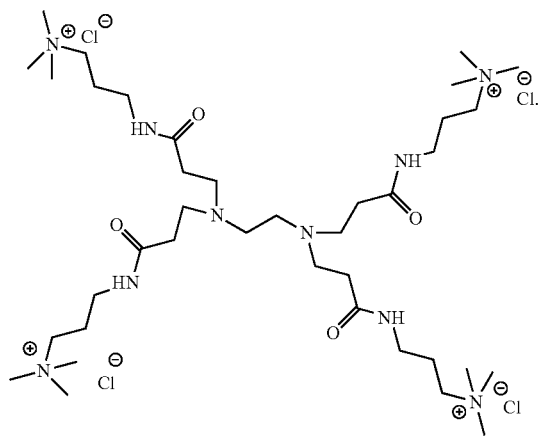

In some other embodiments, the compound is

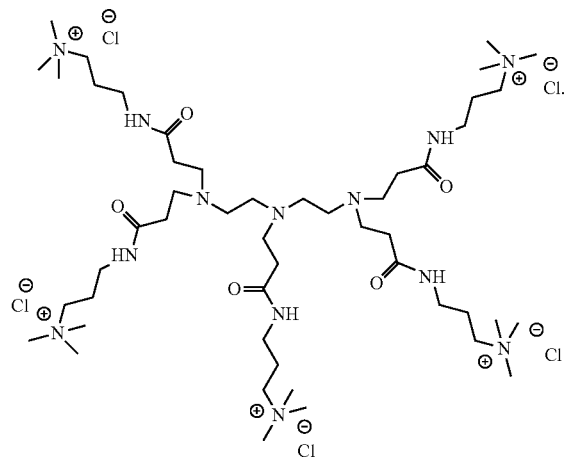

In some other embodiments, wherein the compound is

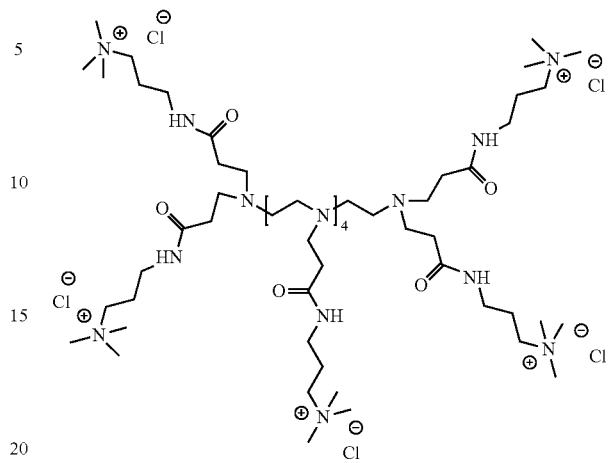

In some embodiments, the multiple charged cationic or anionic compound has an average molecular weight ($M_w$) of from about 100 to about 2,000,000 Da. In some other embodiments, the multiple charged cationic or anionic compound has an average molecular weight ($M_w$) of from about 100 to about 50,000 Da. In yet some other embodiments, the multiple charged cationic or anionic compound has an average molecular weight ($M_w$) of 10 from about 100 Da to about 600 Da, from about 100 Da to about 1,000 Da, from about 100 Da to about 1,400 Da, from about 100 Da to about 3,000 Da, from about 100 Da to about 5,500 Da, or from about 100 Da to about 10,000 Da, from about 100 Da to about 20,000 Da, from about 100 Da to about 30,000 Da, or from about 100 Da to about 40,000 Da.

In some embodiments, the multiple charged cationic compound has at least 2, at least 3, at least 4, at least 5, at least 6, at least 7, at least 8, at least 9, or at least 10 positive charges. In some other embodiments, the compound has from 10 to 1,000 positive charges, or any value there between positive charges.

In some embodiments, the multiple charged cationic compound has at least 2, at least 3, at least 4, at least 5, at least 6, at least 7, at least 8, at least 9, or at least 10 negative charges. In some other embodiments, the compound has from 10 to 1,000 positive charges, or any value there between negative charges.

In some embodiments, the compound is soluble or dispersible in water.

Methods of Making

In another aspect, disclosed here is a method of making a compound or its salt, wherein the method comprises contacting a polyamine with an activated olefin (Michael acceptor) having an ionic group according to one of the following formulas

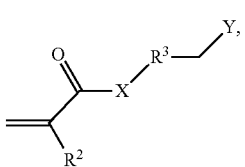

-continued

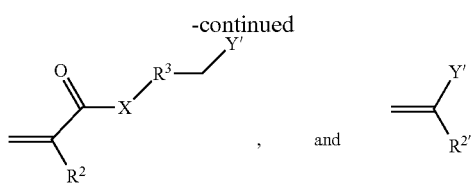 and 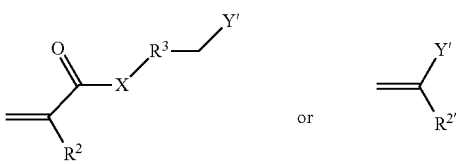

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y'; m is an integer of 2 to 4; $R^3$ is absent or an unsubstituted, linear or branched $C_1$-$C_{30}$ alkylene group; Y is-$NR_4R_5R_6^{(+)}$, Y' is —COOH, —$SO_3$H, —$PO_3$H, —$OSO_3$H, —$OPO_3$H, or a salt thereof, and $R^4$, $R^5$, and $R^6$ are independently a $C_1$-$C_{10}$ alkyl group; wherein the polyamine and the activated olefin undergo aza-Michael addition reaction; and the compound is a multiple charged cationic compound having 2 or more positive charges or multiple charged anionic compound having 2 or more negative charges.

In some embodiments of the disclosed methods, the polyamine is a $NH_2$—$[R^{10}]_n$—$NH_2$, $(RNH)_n$—$RNH_2$, $H_2N$—$(RNH)_n$—$RNH_2$, $H_2N$—$(RN(R'))_n$—$RNH_2$, or a mixture thereof, wherein $R^{10}$ is a linear or branched, unsubstituted or substituted $C_2$-$C_{10}$ alkylene group, or combination thereof; R is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkylene group, or combination thereof; R' is —$CH_2$—, —$CH_2CH_2$—, —$CH_2CH_2CH_2$—, —$CH(CH_3)CH_2$—, a linear or branched, unsubstituted or substituted $C_4$-$C_{10}$ alkyl group, $RNH_2$, $RNHRNH_2$, or $RN(RNH_2)_2$ and n can be from 2 to 1,000,000.

In other embodiments, the activated olefin is

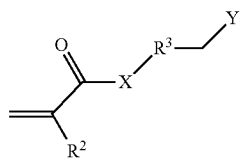

wherein X is NH or O; $R^2$ is H, $CH_3$, or an unsubstituted, linear or branched $C_2$-$C_{10}$ alkyl, alkenyl, or alkynyl group; $R^3$ is absent or an unsubstituted, linear or branched $C_1$-$C_{30}$ alkylene group; Y is-$NR_4R_5R_6^{(+)}$, and $R^4$, $R^5$, and $R^6$ are independently a $C_1$-$C_{10}$ alkyl group.

In some embodiments, the activated olefin activated olefin is (3-acrylamidopropyl)trimethylammonium chloride (APTAC), [3-(methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), 2-(methacryloyloxy)-N,N,N-trimethylethan-1-aminium methyl sulfate (DMAEA-MSQ), or a mixture thereof.

In some embodiments, Y is-$NR_4R_5R_6^{(+)}$ and the counter ion for Y any negative charged ion or species. In some other embodiments, the counter ion for Y is chloride, bromide, fluoride, iodide, acetate, aluminate, cyanate, cyanide, dihydrogen phosphate, dihydrogen phosphite, formate, carbonate, hydrogen carbonate, hydrogen oxalate, hydrogen sulfate, hydroxide, nitrate, nitrite, thiocyanate, or a combination thereof.

In some embodiments of the disclosed methods, the activated olefin is

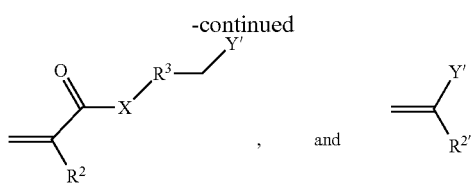 or 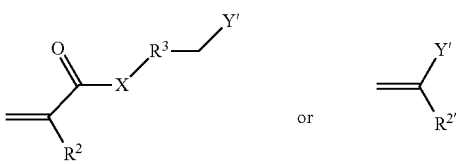

wherein X is NH or O; $R^2$ is H, $CH_3$, or an unsubstituted, linear or branched $C_2$-$C_{10}$ alkyl, alkenyl, or alkynyl group; $R^{2'}$ is H, $CH_3$, or an unsubstituted or substituted, linear or branched $C_1$-$C_{10}$ alkyl, alkenyl, alkynyl group, —COOH, —$CH_2$COOH, Y', or —$(CH_2)_m$—Y'; m is an integer of 2 to 4; $R^3$ is absent or an unsubstituted, linear or branched $C_1$-$C_{30}$ alkylene group; Y' is —COOH, —$SO_3$H, —$PO_3$H, —$OSO_3$H, —$OPO_3$H, or a salt thereof; and $R^4$, $R^5$, and $R^6$ are independently a $C_1$-$C_{10}$ alkyl group.

In some embodiments, the activated olefin is acrylic acid, methacrylic acid, itaconic acid, maleic acid, vinylsulfonic acid, vinylphosphonic acid, or mixture thereof.

In some other embodiments, the activated olefin is 2-acrylamido-2-methylpropane sulfonic acid (AMPS), 3-(allyloxy)-2-hydroxypropane-1-sulfonate, or mixture thereof.

In yet some other embodiments, when the activated olefin contains anionic group that can bear negative charge at an alkaline pH, the counter positive ions for the negative charges include, but are not limited to, alkali metal ions, $Li^+$, $Na^+$, $K^+$, $NH_4^+$, a quaternary ammonium ion, etc.

In some embodiments of the disclosed methods, the contacting step is done in the presence of a reaction solvent. The reaction solvent can be any inorganic or organic solvent commonly used in chemical synthesis. The reaction solvent used in the disclosed method can be introduced into the reaction between the polyamine and the activated olefin including a cationic or anionic group by any way known by one skilled in the art. For example, the solvent can be added into the container or vessel for reaction before, at the same, with one or both reactants, or after the polyamine, the activated olefin, or both are added.

In some embodiments, the reaction solvent is water, methanol, ethanol, propanol, glycol, PEG, or a mixture thereof. In some other embodiments, the reaction solvent is water.

In some other embodiments of the disclosed methods, the contacting step is done in the presence of a catalyst, base, or acid. The catalyst, base, or acid can be introduced into the reaction between the polyamine and activated olefin by any way known by one skilled in the art.

In some embodiments, the contacting step is done without the presence of any additional base or alkalinity source. In some other embodiments, the contacting step is done in the presence of an alkalinity source. In some other embodiments, the contacting step is done in the presence of an organic base, such as alkanolamines. In yet some other embodiments, the contacting step is done in the presence of an alkali metal hydroxide, carbonate, imidazole/pyridine base, or combination thereof, such as NaOH, $Na_2CO_3$, aminoethyl pyridine, aminopropyl imidazole, or a combination thereof. In some other embodiments, the contacting step is done with the presence of benzyltrimethylammonium hydroxide. In some embodiments, the catalyst base is an amidine or guanidine base, or mixtures thereof. In some other embodiments, the catalyst is a ionic liquid, such as 1,8-diazabicyclo[5.4.0]-undec-7-en-8-ium acetate, for the reaction under a solvent free condition at room temperatures.

In yet some other embodiments of the disclosed methods, the contacting step is done in the presence of an acid. In some other embodiments, the contacting step is done in the presence of a catalyst. The catalyst can any one or more of the catalysts known for the Michael addition reaction by one skilled in the art.

In yet some other embodiments of the disclosed methods, the contacting step is done free of a catalyst, base, or acid. In some other embodiments, the contacting step is done free of an alkali metal hydroxide, carbonate, silicate, metasilicate, imidazole/pyridine-based base, or all thereof. In some embodiments, the contact step is done free of a base.

In yet another aspect, disclosed herein is an article, product, or composition comprising one or more compounds disclosed here or produced by the methods disclosed herein.

In some embodiments, the article, product or composition further comprises a carrier solvent or a carrier. As used herein, a "carrier solvent" or carrier is a solvent or solvent system in which the disclosed compound can be distributed evenly and stable.

As used herein, "stable" means that compounds disclosed herein does not precipitate from or separated from the carrier solvent or other ingredients in the composition in about 1 hour, from about 1 hour to about 12 hours, about 12 hours, about 1 day, about 5 days, about 10 days, about 20 days, about 1 month, from about 1 month to about 1 year, or from about 1 year to about 2 year after the compounds disclosed herein and carrier solvent or any other ingredients are mixed homogenously.

In some other embodiments, the carrier is water, an organic solvent, or a mixture thereof. In some embodiments, the article, product, or composition further comprises an organic solvent. In some other embodiments, the article, product, or composition further comprises an organic solvent and water.

In some embodiments, the carrier solvent can be any inorganic or organic solvent commonly used in industry or in laboratory. In some other embodiments of the article, product, or composition, the carrier solvent is water, an alcohol, an alkylene glycol, an alkyleneglycol alkyl ether, or a combination thereof. In some other embodiments, the carrier solvent is methanol, ethanol, propanol, isopropanol, butanol, isobutanol, monoethyleneglycol, ethyleneglycol monobutyl ether, or a combination thereof.

In some embodiments, the articles, products, or compositions are solid. In some other embodiments, the articles, products, or compositions are liquid.

In one aspect, disclosed herein is a composition for resolving a reverse emulsion in a produced fluid from an oil and gas production system, wherein the reverse emulsion breaker composition comprises one or more compounds or their salts disclosed herein and one or more reverse emulsion breaker composition agents. In some embodiments, the reverse emulsion composition breaks oil-in-water emulsion in the produced fluid.

In another aspect, disclosed herein is a method of resolving a reverse emulsion in a produced fluid from an oil and gas production system, wherein the method comprises contacting a produced fluid of an oil and gas production system with a reverse emulsion breaker (REB) composition to generate a treated produced fluid, wherein the reverse emulsion breaker composition comprises one or more compounds disclosed herein and one or more reverse emulsion breaker composition agents. In some embodiments, the reverse emulsion composition breaks oil-in-water emulsion in the produced fluid.

In some embodiments, the produced fluid comprises oil-in-water emulsion, water-in-oil-in-water emulsion, or both. In some other embodiments, the produced fluid comprises crude oil, refined oil, bitumen, condensate, slop oil, distillates, fuels, or mixtures thereof.

In some embodiments, the produced fluid comprises fresh water, recycled water, salt water, surface water, produced water, or mixture thereof. In some embodiments, the produced fluid is one out of petroleum wells, downhole formations, or geothermal wells.

In some embodiments, the produced fluid is from a steam assisted gravity drainage (SAGD) process, and wherein the produced fluid comprises bitumen and water. In some other embodiments, wherein the produced fluid is a produced water, wherein the produced water is water part of the produced fluid after the oil and soils are removed.

In some embodiments, the compound or the modified compound is soluble or dispersible in water or the reverse emulsion breaker composition.

In some embodiments, the reverse emulsion breaker composition further comprises one or more additional reverse emulsion breaker composition agent.

In some embodiments, the reverse emulsion breaker composition comprises a carrier, wherein the carrier is water, an organic solvent, or a mixture thereof.

In some embodiments, the reverse emulsion breaker composition further comprises an organic solvent. In some other embodiments, the reverse emulsion breaker composition further comprises an organic solvent and water.

In some embodiments, the organic solvent is an alcohol, a hydrocarbon, a ketone, an ether, an alkylene glycol, a glycol ether, an amide, a nitrile, a sulfoxide, an ester, or any combination thereof. In some other embodiments, the organic solvent is an alcohol, an alkylene glycol, an alkyleneglycol alkyl ether, or a combination thereof. In yet some embodiments, the organic solvent is methanol, ethanol, propanol, isopropanol, butanol, isobutanol, monoethyleneglycol, ethyleneglycol monobutyl ether, or a combination thereof.

In some embodiments, the organic solvent is methanol, ethanol, propanol, isopropanol, butanol, 2-ethylhexanol, hexanol, octanol, decanol, 2-butoxyethanol, methylene glycol, ethylene glycol, 1,2-propylene glycol, 1,3-propylene glycol, diethyleneglycol monomethyl ether, diethylene glycol monoethyl ether, ethylene glycol monobutyl ether, ethylene glycol dibutyl ether, pentane, hexane, cyclohexane, methylcyclohexane, heptane, decane, dodecane, diesel, toluene, xylene, heavy aromatic naphtha, cyclohexanone, diisobutylketone, diethyl ether, propylene carbonate, N-methylpyrrolidinone, N,N-dimethylformamide, a mixture thereof with water, or any combination thereof.

In some embodiments, wherein the reverse emulsion breaker composition further comprises one or more of corrosion inhibitors. In some embodiments, wherein the reverse emulsion breaker composition further comprises one or more of corrosion inhibitors and a carrier. In some embodiments, the corrosion inhibitor is an imidazoline compound, a pyridinium compound, or a combination thereof.

In some embodiments, the reverse emulsion breaker composition is free of a corrosion inhibitor.

In some embodiments, the reverse emulsion breaker composition further comprises a biocide. In some embodiments, the reverse emulsion breaker composition further comprises a biocide and carrier. In some other embodiments, the reverse emulsion breaker composition further comprises a biocide, corrosion inhibitor, and carrier.

In some other embodiments, the biocide is chlorine, hypochlorite, $ClO_2$, bromine, ozone, hydrogen peroxide, peracetic acid, peroxysulphate, glutaraldehyde, dibromonitrilopropionamide, isothiazolone, terbutylazine, polymeric biguanide, methylene bisthiocyanate, tetrakis hydroxymethyl phosphonium sulphate, and any combination thereof.

In some embodiments, the reverse emulsion breaker composition is free of a biocide.

In some embodiments, the reverse emulsion breaker composition further comprises an organic sulfur compound. In some other embodiments, wherein the organic sulfur compound is a mercaptoalkyl alcohol, mercaptoacetic acid, thioglycolic acid, 3,3'-dithiodipropionic acid, sodium thiosulfate, thiourea, L-cysteine, tert-butyl mercaptan, sodium thiosulfate, ammonium thiosulfate, sodium thiocyanate, ammonium thiocyanate, sodium metabisulfite, or a combination thereof.

In some embodiments, the reverse emulsion breaker composition further comprises an acid. In some embodiments, the reverse emulsion breaker composition further comprises an inorganic acid, mineral acid, organic acid, or mixture thereof. In some embodiments, the reverse emulsion breaker composition comprises from about 1 wt-% to about 20 wt-%, from about 1 wt-% to about 15 wt-%, from about 1 wt-% to about 10 wt-%, from about 1 wt-% to about 5 wt-% of the acid.

In some embodiments, the acid is hydrochloric acid, hydrofluoric acid, citric acid, formic acid, acetic acid, or mixture thereof.

In some embodiments, the reverse emulsion breaker composition further comprises a hydrogen sulfide scavenger. In some other embodiments, the hydrogen sulfide scavenger is an oxidant, inorganic peroxide, sodium peroxide, chlorine dioxide; a $C_1$-$C_{10}$ aldehyde, formaldehyde, glyoxal, glutaraldehyde, acrolein, or methacrolein, a triazine, monoethanolamine triazine, monomethylamine triazine, or a mixture thereof.

In some embodiments, the reverse emulsion breaker composition further comprises a surfactant. In some embodiments, the reverse emulsion breaker composition further comprises a surfactant, biocide, and carrier.

In some embodiments, the surfactant is a nonionic, cationic, anionic, amphoteric, zwitterionic, gemini, di-cationic, di-anionic surfactant, or mixtures thereof.

In some embodiments, the surfactant is an alkyl phenol, fatty acid, or mixture thereof.

In some embodiments, the reverse emulsion breaker composition further comprises an asphaltene inhibitor, a paraffin inhibitor, a scale inhibitor, a gas hydrate inhibitor, a pH modifier, or any combination thereof.

In some embodiments, the reverse emulsion breaker composition further comprises a coagulant/flocculant agent, water clarifier, or mixture thereof. In some embodiments, the reverse emulsion breaker composition further comprises an additional reverse emulsion breaker, carrier, corrosion inhibitor, a coagulant/flocculant agent, water clarifier, or mixture thereof.

In some embodiments, the reverse emulsion breaker composition further comprises an additional reverse emulsion breaker. In some embodiments, the reverse emulsion breaker composition further comprises an additional reverse emulsion breaker, carrier, and corrosion inhibitor.

In some embodiments, the reverse emulsion breaker composition further comprises an additional reverse emulsion breaker, emulsion breaker, or mixture thereof.

In some embodiments, the emulsion breaker or the additional REB is contacted with the produced fluid independently, simultaneously, or sequentially. In some other embodiments, the emulsion breaker or the additional REB contacts with the produced fluid with the multiple charged compound in the REB composition or through another composition.

In some embodiments, the additional reverse emulsion breakers are organic polymers such as acrylic acid-based polymers, acrylamide-based polymers, polymerized amines, alkanolamines, thiocarbamates, and cationic polymers such as acrylamide diallyldimethylammonium chloride (DADMAC) polymer and/or methylacrylamide [3-(Methacryloylamino)propyl]trimethylammonium chloride (MAPTAC) polymers, copolymers of epichlorohydrin and dimethylamine or trimethylamine, copolymers of acrylamide and dimethylaminoethyl acrylate-methyl chloride quaternized, aluminium chlorohydrate (ACH) and polyaluminium chlorides (PAC), acrylamides-DMAEA.MCQ copolymers.

In some embodiments, the reverse emulsion breaker composition further comprises a dispersant.

In some embodiments, the reverse emulsion breaker composition further comprises antioxidant, polymer degradation prevention agent, permeability modifier, foaming agent, antifoaming agent, scavenger agent for $CO_2$, and/or $O_2$, gelling agent, lubricant, friction reducing agent, salt, alkalinity source, or mixture thereof.

In some embodiments, the reverse emulsion breaker composition (REB) is a liquid, gel, or a mixture comprising liquid/gel and solid. In some embodiments, the REB composition is a solid or liquid.

In some embodiments, the reverse emulsion breaker composition or a use solution thereof has a pH of from about 2 to about 11.

In some embodiments, the reverse emulsion breaker composition comprises from about 10 wt-% to about 80 wt-% of the multiple charged cationic or anionic compound disclosed herein or salt thereof. In some embodiments, the REB composition comprises from about 30 wt-% to about 70 wt-%, from about 20 wt-% to about 40 wt-%, from about 25 wt-% to about 30 wt-%, from about 10 wt-% to about 70 wt-%, from about 30 wt-% to about 60 wt-%, from about 40 wt-% to about 50 wt-%, from about 10 wt-% to about 30 wt-%, from about 20 wt-% to about 40 wt-%, from 30 wt-% to about 50 wt-%, from about 40 wt-% to about 60 wt-%, from about 50 wt-% to 70 wt-%, about 10 wt-%, 15 wt-%, 20 wt-%, 25 wt-%, 30 wt-%, 35 wt-%, 40 wt-%, 45 wt-%, 50 wt-%, 55 wt-%, 60 wt-%, 65 wt-%, 70 wt-%, 75 wt-%, or any value there between of the multiple charged cationic or anionic compound disclosed herein or salt thereof.

In some embodiments, the multiple charged cationic or anionic compound disclosed herein or salt thereof has a concentration of from about 1 ppm to about 200 ppm in the treated produced fluid. In the other embodiments, wherein the multiple charged cationic or anionic compound has a concentration of from about 10 ppm to about 150 ppm in the treated produced fluid after the REB composition is applied to the produced fluid. In yet some other embodiments, the compound has a concentration of from about 10 ppm to about 75 ppm in the treated produced fluid after the REB composition is applied to the produced fluid.

Use of the Methods or Compositions Disclosed

In some embodiments, for the methods disclosed herein, providing a REB composition into a produced fluid means that the REB composition or multiple charged cationic or anionic compounds, or use solution thereof is added into a produced fluid. In some other embodiments, providing a REB composition into a produced fluid means adding the REB composition or multiple charged cationic or anionic compounds to a fluid which contacts or makes the produced fluid. The REB composition or multiple charged cationic or anionic compounds, or use solution thereof may be added continuously, or intermittently when more compounds or compositions may be needed.

A use solution of a REB composition or multiple charged cationic or anionic compounds as used herein refers to a diluted solution for the composition or compounds by a diluent. A diluent as used herein refers to water, a produced fluid, or one of the carriers or solvents defined herein. The REB composition or the compounds can be diluted by a factor of 0.5, 1, 2, 3, 4, 5, 6, 7, 8, 9, 10, 11-1,000,000, or any value there between to generate a use solution and then provide the use solution to a produced fluid. In this disclosure, when a REB composition or multiple charged cationic or anionic compounds are applied, either the composition/compounds or use solution thereof is applied.

In some embodiments, the reverse emulsion breaker composition is provided to the water system independently, simultaneously, or sequentially with one or more additional reverse emulsion breaker composition agents in the REB composition.

In some embodiments, the REB composition is diluted with water to create a use solution of the REB composition, the use solution is then provided into the produced fluid. In some other embodiments, the water to dilute the REB composition comprises fresh water, recycled water, salt water, surface water, produced water, or mixture thereof. In some embodiments, the water to dilute the REB composition is the produced fluid.

Usually, the REB composition or its use solution is injected into the produced fluid. In this situation, the produced fluid is the use solution of the REB compositions. In some embodiments, the concentration of the REB composition is from about 1 ppm to about 1,000 ppm.

In some embodiments, the additional REB, flocculant, coagulant, or water clarifier is a terpolymer comprising

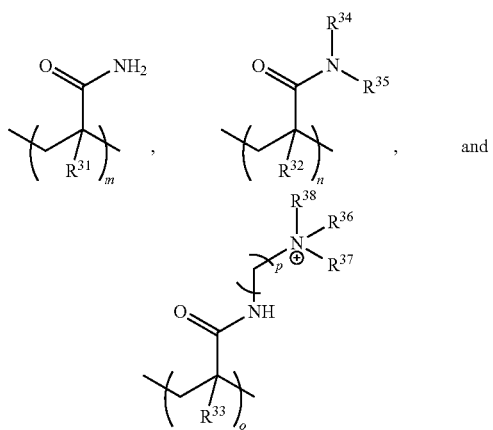

monomers and having an average molecular weight ($M_w$) of from about 20,000 to about 20,000,000 Da, wherein $R^{31}$, $R^{32}$, and $R^{33}$ are independently hydrogen or an alkyl; $R^{34}$, $R^{35}$, $R^{36}$, $R^{37}$, and $R^{38}$ are independently an alkyl; p is an integer from 1 to 6; and m, n, and o are integers.

In some embodiments, the emulsion breaker, REB, flocculant, coagulant, or water clarifier is another polymeric cationic, anionic, nonionic, inorganic coagulant/flocculant agent.

In some embodiments, the emulsion breaker, REB, flocculant, coagulant, or water clarifier is an oxyalkylated phenol-formaldehyde resin, a resin ester, an oxyalkylated polyalkylamine, a polyol, a cross-linked polyol with a di- or multi-functional cross linker, an isocyanate, an acid, or a combination thereof.

In some embodiments, the emulsion breaker, REB, flocculant, coagulant, or water clarifier is aluminum sulfate, aluminum chloride, ferric sulfate, ferric chloride, calcium hydroxide, calcium oxide, sodium carbonate, potassium carbonate, magnesium oxide, magnesium hydroxide, or mixture thereof.

In some embodiments, the emulsion breaker, REB, flocculant, coagulant, or water clarifier is a dendritic polyamine, dendritic polyamidoamine, hyperbranched polyethyleneimine, a reaction product thereof with gluconolactone, alkylene oxide, 3-chloro-2-hydroxypropanesulfonic acid, alkyl halide, benzyl halide and dialkyl sulfate, or mixture thereof.

In some embodiments, the emulsion breaker, REB, flocculant, coagulant, or water clarifier is a polyepihalohydrin, polyelectrolyte thereof, or mixture thereof.

In some embodiments, the emulsion breaker, REB, flocculant, coagulant, or water clarifier is a tridithiocarbamicacid, dithiocarbamic salt, dimethylaminoethyl acrylate methyl chloride, benzyl chloride quaternary salt, polymeric quaternary ammonium betaines, metal salt, zinc chloride, aluminum chloride, polymeric quaternary ammonium salt, copolymer of acrylic acid and acrylamide, or mixture thereof.

In some embodiments, the emulsion breaker, REB, flocculant, coagulant, or water clarifier is a high molecular weight polymeric cationic coagulant/flocculant agent and wherein the high molecular weight polymeric cationic coagulant/flocculant agent has an average molecular weight ($M_w$) of from 100,000 to 2,000,000 Da. In some embodiments, the high molecular weight polymeric cationic coagulant/flocculant agent has average net charges of from 10 to 1,000.

In some embodiments, the emulsion breaker, REB, flocculant, coagulant, or water clarifier is a low molecular weight polymeric cationic coagulant/flocculant agent and wherein the low molecular weight polymeric cationic coagulant/flocculant agent has an average molecular weight ($M_w$) of from 10,000 to 100,000 Da. In some embodiments, the low molecular weight polymeric cationic coagulant/flocculant agent has net charges of from 3 to 10.

In some embodiments, the emulsion breaker, REB, flocculant, coagulant, or water clarifier is a high molecular weight polymeric anionic coagulant/flocculant agent and wherein the high molecular weight polymeric cationic coagulant/flocculant agent has a molecular weight of from 100,000 to 2,000,000. In some other embodiments, the emulsion breaker, REB, flocculant, coagulant, or water clarifier is a low molecular weight polymeric anionic coagulant/flocculant agent and wherein the low molecular weight polymeric anionic coagulant/flocculant agent has a molecular weight of from 10,000 to 100,000.

In some embodiments, the high molecular weight polymeric anionic coagulant/flocculant agent has net charges of from 10 to 1,000. In some other embodiments, the low molecular weight polymeric anionic coagulant/flocculant agent has net charges of from 3 to 10.

In some embodiments, the emulsion breaker, REB, flocculant, coagulant, or water clarifier is a high molecular weight polymeric coagulant/flocculant agent and wherein the high molecular weight polymeric nonionic coagulant/flocculant agent has a molecular weight of from 100,000 to 2,000,000.

In some embodiments, the emulsion breaker, REB, flocculant, coagulant, or water clarifier is a low molecular weight polymeric coagulant/flocculant agent and wherein the low molecular weight polymeric nonionic coagulant/flocculant agent has a molecular weight of from 10,000 to 100,000.

In some embodiments, the reverse emulsion breaker composition comprises one or more multiple charged cationic or anionic compounds, one or more emulsion breaker agents, and one or more diluents.

In some embodiments, wherein the method further comprises separating oil and solid from water in the treated produced fluid through filtration, settling, desalting, electrochemical techniques, centrifugation, flotation, or a combination thereof.

In some embodiments, the REB composition or multiple charged cationic or anionic compounds disclosed herein can breaks oil-in-water emulsion in the produced fluid as indicated a conventional bottle test as described in the Examples section of this disclosure, when the produced fluid has a charge cationic or anionic compound or mixture thereof concentration of from about 1 ppm to about 200 ppm, from about 10 to about 200 ppm, from about 10 ppm to about 150 ppm, from about 10 ppm to about 75 ppm, from about 10 ppm to about 100 ppm, from about 10 ppm to about 120 ppm, about 200 ppm, about 180 ppm, about 160 ppm, about 140 ppm, about 120 ppm, about 100 ppm, about 80 ppm, about 60 ppm, about 50 ppm, about 40 ppm, or any value there between, after dosing the produced fluid with the multiple charged cationic or anionic compound or mixture thereof or the REB composition.

As used herein, the term "substantially free", "free" or "free of" refers to compositions completely lacking the component or having such a small amount of the component that the component does not affect the performance of the composition. The component may be present as an impurity or as a contaminant and shall be less than about 0.5 wt-%. In another embodiment, the amount of the component is less than about 0.1 wt-% and in yet another embodiment, the amount of component is less than about 0.01 wt-%.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present disclosure may comprise, consist essentially of, or consist of the components and ingredients of the disclosed compositions or methods as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

EXAMPLES

Embodiments of the present disclosure are further defined in the following non-limiting Examples. These Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.

Example 1

Synthesis of Multiple Charged Cationic Compound 1

(3-acrylamidopropyl) trimethylammonium chloride (APTAC, 75%, 96 grams) and water (20 grams) were charged into a 250-mL three-necked RBF equipped with magnetic stir bar, temperature probe, and condenser. Tetraethylenepentamine (TEPA, 12 grams) was then added to the well-stirred reaction mixture at room temperature. Reaction temperature was raised to 80° C. and stirred overnight or until the >98% consumption of APTAC. The progression of reaction was monitored by ESI-MS and/or NMR spectroscopy for consumption of the monomer. The resulting aqueous solution of Compound 1 was used as-is for its application testing as REB.

Example 2

Synthesis of Multiple Charged Cationic Compound 2

Ethyleneamine E-100 from Huntsman was used for this reaction. E-100 is a mixture of tetraethylenepentamine (TEPA), pentaethylenehexamine (PEHA), hexaethyleneheptamine (HEHA), and other higher molecular weight amines. E-100 is a complex mixture of various linear, cyclic, and branched amines with a number-average molecular weight ($M_n$) of 250-300 g/mole.

(3-acrylamidopropyl) trimethylammonium chloride (APTAC, 75%, 60 grams) and water (20 grams) were charged into a 250-mL three-necked RBF equipped with magnetic stir bar, temperature probe, and condenser. Ethyleneamine E-100 (12 grams) was then added to the well-stirred reaction mixture at room temperature. Reaction temperature was raised to 80° C. and stirred overnight or until the >98% consumption of APTAC. The resulting aqueous solution of Compound 2 was used as-is for application testing.

Example 3

Synthesis of Multiple Charged Cationic Compound 3

(3-acrylamidopropyl) trimethylammonium chloride (APTAC, 75%, 70 grams) and water (20 grams) were charged into a 250-mL three-necked RBF equipped with magnetic stir bar, temperature probe, and condenser. Pentaethylenehexamine (PEHA, 10 grams, 99%) was then added to the well-stirred reaction mixture at room temperature. Reaction temperature was raised to 80° C. and stirred overnight or until the >98% consumption of APTAC. The resulting aqueous solution of Compound 3 was used as-is for application testing.

Example 4

Synthesis of Multiple Charged Cationic Compound 4

(3-Acrylamidopropyl) trimethylammonium chloride (AP-TAC, 75%, 130 grams) and water (20 grams) were charged into a 250-mL three-necked RBF equipped with magnetic stir bar, temperature probe, and condenser. Diethylenetriamine (DETA, 10 grams) was then added to the well-stirred reaction mixture at room temperature. Reaction temperature was raised to 80° C. and stirred overnight or until the >98% consumption of APTAC. Reaction temperature was raised to 80° C. and stirred overnight or until the >98% consumption of APTAC. The resulting aqueous solution of Compound 4 was used as-is for application testing.

Example 5

Synthesis of Multiple Charged Cationic Compound 5

BASF Lupasol G20 (50% aqueous solution of polyethyleneimine with a weight-average molecular weight ($M_w$) around 1,300 g/mole) was used for this reaction.

(3-acrylamidopropyl) trimethylammonium chloride (APTAC, 75%, 78.55 grams) was charged into a 250-mL three-necked RBF equipped with magnetic stir bar, temperature probe, and condenser. Lupasol G20 (50%, 50 grams) was then added to the well-stirred reaction mixture at room temperature. Reaction temperature was raised to 80° C. and stirred overnight or until the >98% consumption of APTAC. The resulting aqueous solution of Compound 5 was used as-is for application testing.

Example 6

Synthesis of Multiple Charged Cationic Compound 6

BASF Lupasol G100 (50% aqueous solution of a polyethyleneimine with a weight-average molecular weight ($M_w$) around 5000 g/mole) was used for this reaction.

(3-Acrylamidopropyl) trimethylammonium chloride (APTAC, 75%, 72.4 grams) was charged into a 250-mL three-necked RBF equipped with magnetic stir bar, temperature probe, and condenser. Lupasol G100 (50%, 50 grams) was then added to the well-stirred reaction mixture at room temperature. Reaction temperature was raised to 80° C. and stirred overnight or until the >98% consumption of APTAC. The resulting aqueous solution of Compound 6 was used as-is for application testing.

Example 7

Effect of Some Exemplary Multiple Charged Cationic Polyamines For Breaking Emulsion in A Produced Fluid

The efficacy of some exemplary multiple charged cationic compounds was tested using the produced fluids from three different sites. The sample ID and structure of the exemplary multiple charged cationic compounds is listed in Table 2.

TABLE 2

Compound ID and Structures of the Exemplary Multiple Charged Cationic Compounds

| Compound ID | Polyamine | Activated Olefin |
|---|---|---|
| 1 | Tetraethylenepentamine | APTAC |
| 2 | Ethyleneamine E-100 | APTAC |
| 3 | Pentaethylenehexamine | APTAC |
| 4 | Diethylenetriamine | APTAC |
| 5 | Lupasol ® G20 | APTAC |
| 6 | Lupasol ® G100 | APTAC |

The efficacy of a REB is usually measured by the emulsion stability of the produced fluids to which the REB in a specific concentration is added to, in a simulated condition that matches closely to the production site.

Emulsion stability is monitored by measuring phase separation up to 90° C. using conventional bottle testing. The produced fluid, e.g., emulsion solution (100 mL) is poured in a 6-ounce prescription glass bottle and heated to the system temperature of interest in a water bath. A diluent is usually added to the emulsion at some point in the method and mixed using a mechanical shaker at low speed for five minutes or mixed by shaking the bottle by hand.

The bottle testing was done using a high temperature bottle test equipment. This bottle test equipment can achieve the high temperature and pressure conditions that matches conventional methods for the oil/water separation at any specific production site. Although the bottle test equipment is a very simple treating system and does not exactly duplicate what happens in a complex treating system that uses separators, wash tanks, heater treaters, etc. at an oil production facility, it does enable one to compare the test results with those at the facility. For example, if the oil out of the treating system contains only 0.5% BS&W (Bitumen, Solid and Water emulsion), then our oil analysis from the bottle test for a REB should also be close to this result.

There is no standard bottle test condition because each customer's equipment, its arrangement, distances; temperature, and chemical injection points differ. However, the bottle test equipment used in this example can adjust the chemical ratio, agitation, temperature, and settling time to match a production facility's conditions.

Produced fluids were collected from a customer's process for use in this example. Some aging of the sample occurred; however, time to transfer into bottles and begin testing was minimized in this work to reduce variation of results. Diluent samples were collected and used over multiple days.

For a bottle test, about 100 ml of a sample was added to the bottles. EB was then injected (rate based on oil cut) into the bottles, which then were sealed and placed into the bottle test equipment. The samples were then heated to a temperature, such as, 140° C., and bottles were agitated using a mechanical shaker. REB and diluent were injected into the bottles and various agitation stages completed. Water drop readings were taken over the course of a predetermined time and recorded in mL, then a top oil sample was drawn at test temperature and pressure using a syringe. This oil sample was added to a centrifuge tube containing xylene, toluene, or mineral spirits (e.g., Varsol™). The mixture was shaken well to mix and then centrifuged. BS&W was then measured. Water quality was inspected using a variety of techniques including visual inspection and turbidity. Usually, composites samples were measured for emulsion by removing of free water, gently mixing, then transferring to centrifuge tubes with xylene, toluene, or mineral spirits (e.g., Varsol™). Samples were well shaken to mix well, then centrifuged and BS&W was recorded.

Water clarity was ranked on a comparative visual scale from 11 (partially broken reverse) to a 1 (about 50 NTU). A rating of 9 could be deemed equivalent to 1500 NTU, while a rating of 4 or 5 would be equal to about 500 NTU.

The test results for the exemplary multiple charged polyamines and some existing REBs are shown in Table 4, Table 5, and Tables 6A-6B for the tests at three different sites, respectively. In Table 4, Table 5, and Tables 6A-6B, G=good, F=fair, P=poor, and VP=very poor. The "+" or "−" is the additional modifiers for "G", "P", and "VP."

TABLE 4

Emulsion Stability Test Results with a produced fluid from Site 1

| Site | Compound ID | REB rate (ppm) | Effect | Water Quality | Turbidity (NTU) |
|---|---|---|---|---|---|
| Site 1 | 1 | 50 | reverse broken | F− | 437 |
| Site 1 | 1 | 100 | reverse broken | F | 431 |
| Site 1 | 2 | 50 | reverse broken | F+ | 292 |
| Site 1 | 2 | 100 | reverse broken | F | 404 |
| Site 1 | 3 | 50 | reverse broken | G | 333 |
| Site 1 | 3 | 100 | reverse broken | F | 372 |
| Site 1 | 4 | 50 | reverse broken | F | 391 |
| Site 1 | 4 | 100 | reverse broken | G | 293 |
| Site 1 | 1 | 50 | reverse broken | F+ | 338 |
| Site 1 | 1 | 100 | reverse broken | F | 392 |
| Site 1 | 2 | 50 | reverse broken | F+ | 357 |
| Site 1 | 2 | 100 | reverse broken | F+ | 336 |
| Site 1 | 3 | 50 | reverse broken | F+ | 344 |
| Site 1 | 3 | 100 | reverse broken | G | 340 |
| Site 1 | 4 | 50 | reverse broken | G | 350 |
| Site 1 | 4 | 100 | reverse broken | G | 307 |
| Site 1 | 2 | 25 | reverse broken | F | 341 |
| Site 1 | 3 | 25 | reverse broken | F | 381 |
| Site 1 | 4 | 25 | reverse broken | F− | 412 |
| Site 2 | 5 | 50 | reverse broken | F− | 408 |
| Site 2 | 5 | 50 | reverse broken | F+ | 513 |
| Site 2 | 5 | 50 | reverse broken | G | 534 |
| Site 2 | 5 | 25 | reverse broken | F− | 380 |
| Site 2 | 5 | 50 | reverse broken | F | 481 |
| Site 2 | 5 | 100 | reverse broken | F− | 510 |
| Site 2 | 2 | 25 | reverse broken | F− | 378 |
| Site 2 | 2 | 50 | reverse broken | G | 389 |
| Site 2 | 2 | 100 | reverse broken | F− | 393 |
| Site 2 | 6 | 25 | reverse broken | P | 350 |
| Site 2 | 6 | 50 | reverse broken | P | 501 |
| Site 2 | 6 | 100 | reverse broken | VP | 463 |
| Site 2 | 5 | 25 | reverse broken | F− | 363 |
| Site 2 | 5 | 50 | reverse broken | F− | 437 |
| Site 2 | 5 | 100 | reverse broken | F− | 519 |
| Site 2 | 2 | 25 | reverse broken | F− | 319 |
| Site 2 | 2 | 100 | reverse broken | F | 381 |
| Site 2 | 2 | 50 | reverse broken | F | 393 |

TABLE 5

Emulsion Stability Test Results with a produced fluid from Site 2

| Compound ID | REB rate (ppm) | Effect | 30 min water drop | 60 min water drop | Water Quality | Water Quality | Visual |
|---|---|---|---|---|---|---|---|
| 5 | 150 | reverse broken | 10 | 50 | F | 308 | 13.9% |
| 6 | 150 | reverse broken | 20 | 20 | F | 288 | 13.0% |
| 1 | 150 | reverse broken | 78 | 78 | F | 168 | 7.6% |
| 2 | 150 | reverse broken | 20 | 30 | F | 180 | 8.1% |
| 3 | 150 | reverse broken | 79 | 79 | F | 186 | 8.4% |
| 4 | 150 | reverse broken | 30 | 30 | VP | 0 | 0.0% |

TABLE 6A

Emulsion Stability Test Results with a produced fluid from Site 3

| Compound ID | REB Ratio (ppm) | Effect | 30 min. water drop (ml) | 60 min. water drop (ml) | 120 min. water drop (ml) | Water removed |
|---|---|---|---|---|---|---|
| 1 | 15 | no treat | 60 | 65 | 70 | 54 |
| 1 | 30 | reverse broken | 10 | 30 | 40 | 60 |
| 1 | 50 | reverse broken | 0 | 15 | 40 | 48 |
| 1 | 50 | reverse broken | 50 | 70 | 65 | 62 |
| 3 | 15 | no treat | 68 | 70 | 70 | 56 |
| 3 | 30 | reverse broken | 60 | 68 | 68 | 60 |
| 3 | 50 | reverse broken | 60 | 70 | 70 | 60 |

TABLE 6B

Emulsion Stability Test Results with a produced fluid from Site 3

| Compound ID | REB Ratio (ppm) | Water Quality | Top Oil BS (%) | Top Oil H₂O (%) | Composite BS (%) | Composite H₂O (%) |
|---|---|---|---|---|---|---|
| 1 | 15 | VP | 1 | 0.2 | 5.5 | 11 |
| 1 | 30 | P | 1 | 0.2 | 8 | 10 |
| 1 | 50 | F+ | 0.7 | 0.05 | 4 | 11 |
| 1 | 50 | F+ | 0.3 | 0 | 0.8 | 4.4 |
| 3 | 15 | P | 0.2 | 0.1 | 0.8 | 2 |
| 3 | 30 | G+ | 0.2 | 0.05 | 1 | 9 |
| 3 | 50 | G | 0.2 | 0.05 | 0.5 | 6 |

Example 8

Synthesis of Multiple Charged Cationic Compound 7

(3-Acrylamidopropyl) trimethylammonium chloride (APTAC, 75%, 100 grams) was charged into a 250-mL three-necked RBF equipped with magnetic stir bar, temperature probe, and condenser. Triethylenetetramine (TETA, 60%, 15 grams) was then added to the well-stirred reaction mixture at room temperature. Reaction temperature was raised to 80° C. and stirred overnight or until the >98% consumption of APTAC. The resulting aqueous solution of Compound 7 was used as-is for application testing.

Example 9

Synthesis of Multiple Charged Cationic Compound 8

(3-Acrylamidopropyl) trimethylammonium chloride (APTAC, 75%, 216 grams) was charged into a 250-mL three-necked RBF equipped with magnetic stir bar, temperature probe, and condenser. Tris(2-aminoethyl)amine (95%, 216 grams) was then added to the well-stirred reaction mixture at room temperature. Reaction temperature was raised to 80° C. and stirred overnight or until the >98% consumption of APTAC. The resulting aqueous solution of Compound 8 was used as-is for application testing.

Example 10

Synthesis of Multiple Charged Cationic Compound 9

(3-Acrylamidopropyl) trimethylammonium chloride (APTAC, 75%, 199 grams) was charged into a 250-mL three-necked RBF equipped with magnetic stir bar, temperature probe, and condenser. Ethylenediamine (EDA, 99%, 11 grams) was then added to the well-stirred reaction mixture at room temperature. Reaction temperature was raised to 80° C. and stirred overnight or until the >98% consumption of APTAC. The resulting aqueous solution of Compound 9 was used as-is for application testing.

Example 11

Synthesis of Multiple Charged Cationic Compound 10

2-acrylamido-2-methylpropane sulfonic acid sodium salt (NaAMPS, 58%, 94 grams) was charged into a 250-mL three-necked RBF equipped with magnetic stir bar, temperature probe, and condenser. Diethylenediamine (DETA, 99%, 5 grams) was then added to the well-stirred reaction mixture at room temperature. Reaction temperature was raised to 80° C. and stirred overnight or until the >98% consumption of NaAMPS. The resulting aqueous solution of Compound 10 was used as-is for application testing.

Example 12

Synthesis of Multiple Charged Cationic Compound 11

2-acrylamido-2-methylpropane sulfonic acid sodium salt (NaAMPS, 58%, 70 grams) was charged into a 250-mL three-necked RBF equipped with magnetic stir bar, temperature probe, and condenser. Triethylenepentaamine (TEPA, 99%, 5 grams) was then added to the well-stirred reaction mixture at room temperature. Reaction temperature was raised to 80° C. and stirred overnight or until the >98% consumption of NaAMPS. The resulting aqueous solution of Compound 11 was used as-is for application testing.

Example 13

Synthesis of Multiple Charged Cationic Compound 12

2-acrylamido-2-methylpropane sulfonic acid sodium salt (NaAMPS, 58%, 50 grams) was charged into a 250-mL three-necked RBF equipped with magnetic stir bar, temperature probe, and condenser. Ethylenediamine (99%, 50 grams) was then added to the well-stirred reaction mixture at room temperature. Reaction temperature was raised to 80° C. and stirred overnight or until the >98% consumption of NaAMPS. The resulting aqueous solution of Compound 12 was used as-is for application testing.

Example 14

Synthesis of Multiple Charged Cationic Compound 13

2-acrylamido-2-methylpropane sulfonic acid sodium salt (NaAMPS, 58%, 9.5 grams) was charged into a 250-mL three-necked RBF equipped with magnetic stir bar, temperature probe, and condenser. Tris(2-aminoethyl)amine (95%, 145 grams) was then added to the well-stirred reaction mixture at room temperature. Reaction temperature was raised to 80° C. and stirred overnight or until the >98% consumption of NaAMPS. The resulting aqueous solution of Compound 13 was used as-is for application testing.

Example 15

Synthesis of Multiple Charged Cationic Compound 14

Vinyl sulfonic acid sodium salt (NaVS, 25%, 152 grams) solution was charged into a 250-mL three-necked RBF equipped with magnetic stir bar, temperature probe, and condenser. Diethylenediamine (99%, 6 grams) was then added to the well-stirred reaction mixture at room temperature. Reaction temperature was raised to 80° C. and stirred overnight or until the >98% consumption of NaVS. The resulting aqueous solution of Compound 14 was used as-is for application testing.

Example 16

Synthesis of Multiple Charged Cationic Compound 15

Vinyl sulfonic acid sodium salt (NaVS, 25%, 113 grams) solution was charged into a 250-mL three-necked RBF equipped with magnetic stir bar, temperature probe, and condenser. Ethyleneamine E-100 (99%, 9 grams) was then added to the well-stirred reaction mixture at room temperature. Reaction temperature was raised to 80° C. and stirred overnight or until the >98% consumption of NaVS. The resulting aqueous solution of Compound 15 was used as-is for application testing.

The disclosures being thus described, it will be obvious that the same may be varied in many ways. Such variations are not to be regarded as a departure from the spirit and scope of the disclosures and all such modifications are intended to be included within the scope of the following claims.

What is claimed is:

1. A method of synthesizing a multiple charged cationic compound, comprising:
contacting a polyamine with an activated olefin having an ionic group to generate a compound;
wherein the polyamine is diethylenetriamine, triethylenetetramine, pentaethylenehexamine, hexaethyleneheptamine, tris(2-aminoethyl)amine, tetraethylenepentamine, polyethyleneeimine, or a combination thereof,
wherein the activated olefin is (3-acrylamidopropyl)trimethylammonium chloride (APTAC), [3-(methacryloylamino)propyl]trimethylammonium chloride (MAPTAC), 2-(acryloyloxy)-N,N,N-trimethylethanaminium chloride (DMAEA-MCQ), N,N-dimethylaminoethyl acrylate benzyl chloride quaternary salt (DMAEA-BCQ), or 2-(methacryloyloxy)-N,N,N-trimethylethan-1-aminium methyl sulfate (DMAEA-MSQ), or a combination thereof,
wherein the polyamine and activated olefin undergo an aza-Michael addition reaction; and
wherein the multiple charged cationic compound is a compound according to the structures:

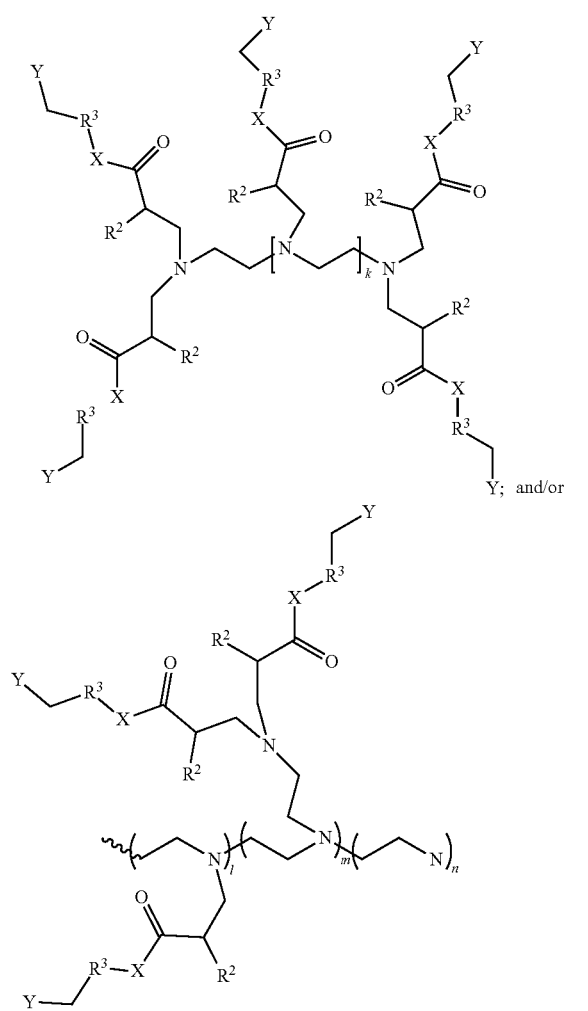

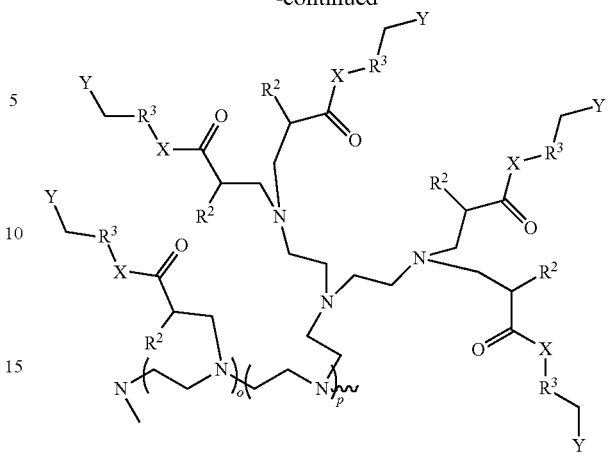

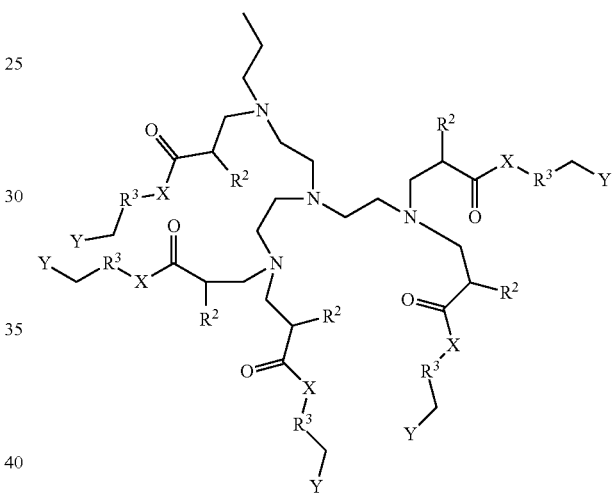

wherein k is an integer of 1-1000; wherein l, m, n, o, or p are each an integer of 0-100 provided that at least one of l, m, n, o, or p is an integer of at least 1; X is NH or O; $R^2$ is H, $CH_3$, or an unsubstituted, linear or branched $C_2$-$C_{10}$ alkyl group; $R^3$ is absent or an unsubstituted, linear or branched $C_1$-$C_{30}$ alkylene group; Y is $-NR^4R_5R^{6(+)}$ or a salt thereof; $R^4$, $R^5$, and $R^6$ are independently a $C_1$-$C_{10}$ alkyl group or benzyl group.

2. The method according to claim 1, wherein the contacting step is done in the presence of a reaction solvent, of a reaction solvent and alkalinity source, of a reaction solvent and acid, or of a reaction solvent and a catalyst.

3. The method according to claim 2, wherein the reaction solvent is water, methanol, ethanol, propanol, glycol, PEG, or a mixture thereof.

4. The method according to claim 1, wherein the contacting step is done in the presence of a reaction solvent and in the absence of an alkalinity source, an acid, and a catalyst.

5. The method according to claim 1, wherein the multiple charged cationic compound is one or more of:

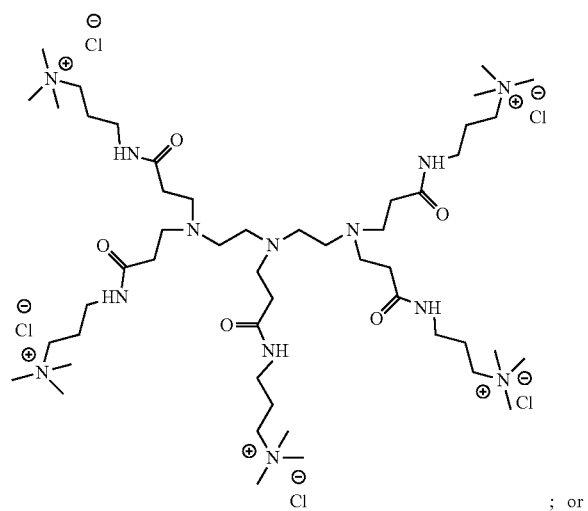

; or

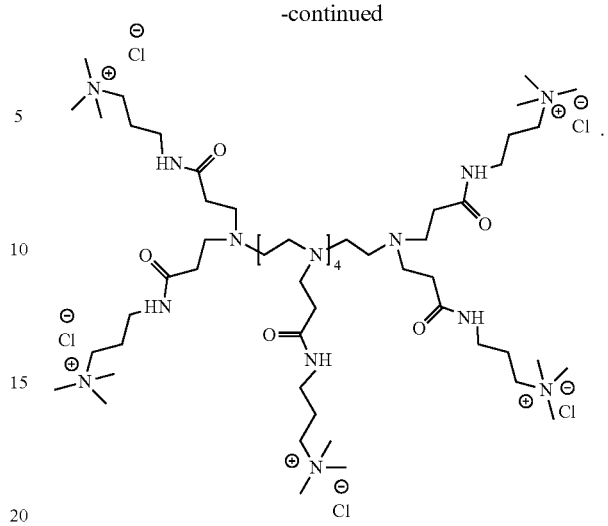

6. The method of claim 2, wherein the catalyst comprises an amidine, guanidine, ionic liquid, or a combination thereof.

7. The method of claim 1, wherein the contacting of the polyamine and the activated olefin occurs at room temperature.

8. The method of claim 7, further comprising a step of increasing the temperature to between 80° C. and 140° C.

9. The method of claim 8, wherein the increasing of the temperature results in >98% consumption of the activated olefin.

10. The method of claim 1, wherein a composition comprising the multiple charged cationic compound does not experience precipitation or phase separation for a period of between about 1 hour to about 2 years.

11. The method of claim 1, wherein the multiple charged cationic compound is:

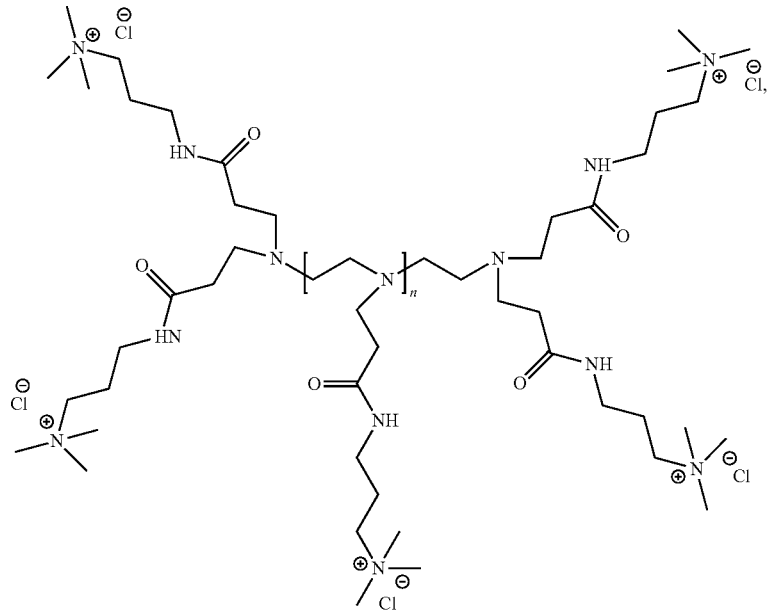

-continued
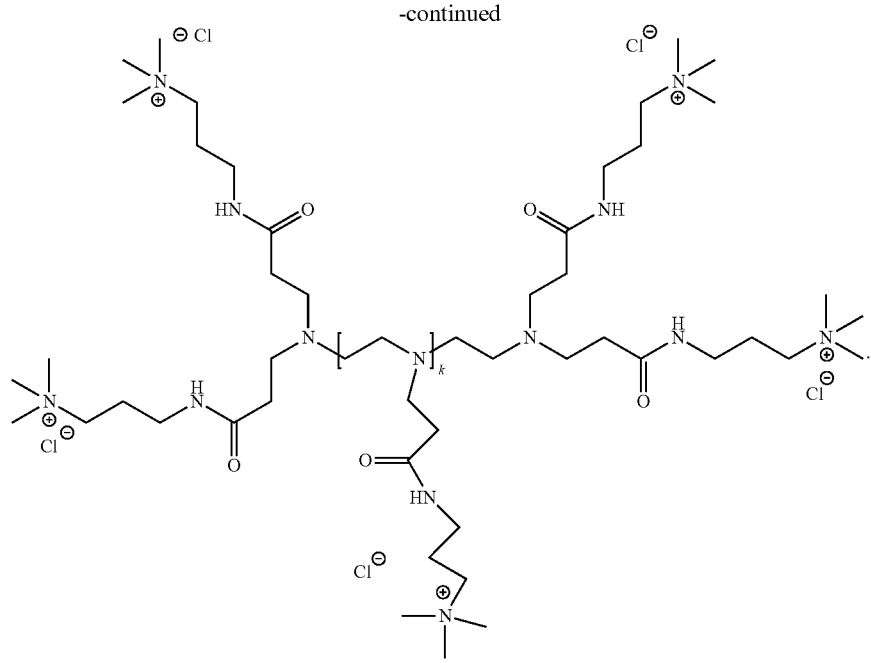
wherein k=1-1000.
* * * * *

UNITED STATES PATENT AND TRADEMARK OFFICE
CERTIFICATE OF CORRECTION

Page 1 of 4

PATENT NO. : 11,685,709 B2
APPLICATION NO. : 16/554935
DATED : June 27, 2023
INVENTOR(S) : Ashish Dhawan, Keith A. Monk and Carter M. Silvernail It is certified that error appears in the above-identified patent and that said Letters Patent is hereby corrected as shown below:

In the Claims

In Column 55, Claim 1, Line 14:
DELETE: "thereof," after combination
INSERT: --thereof;-- after combination In Column 55, Claim 1, Line 22:
DELETE: "thereof," after combination
INSERT: --thereof;-- after combination In Column 55, Claim 1, Lines 27-47:

DELETE: " 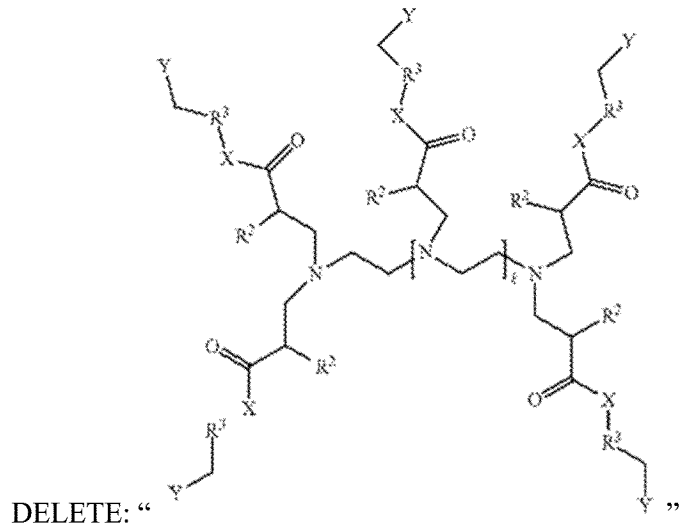 "

Signed and Sealed this
Twenty-sixth Day of December, 2023

Katherine Kelly Vidal
*Director of the United States Patent and Trademark Office*

CERTIFICATE OF CORRECTION (continued)
U.S. Pat. No. 11,685,709 B2

INSERT: --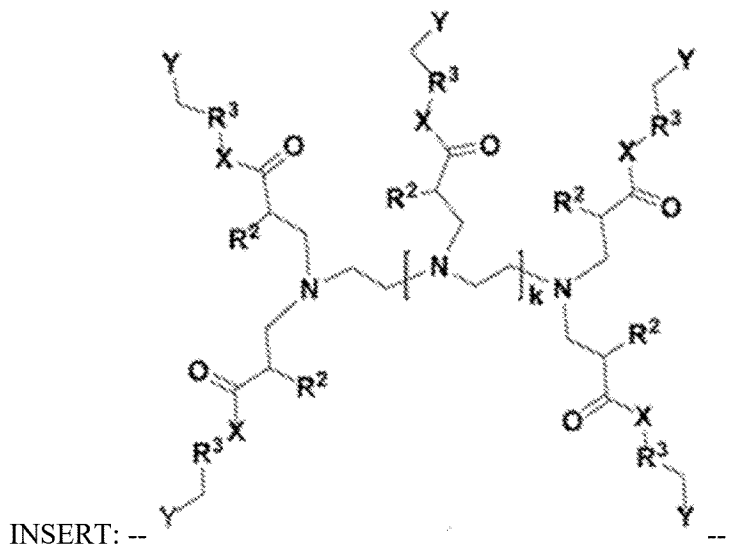--

In Column 55, Claim 1, Lines 47-66:

DELETE: "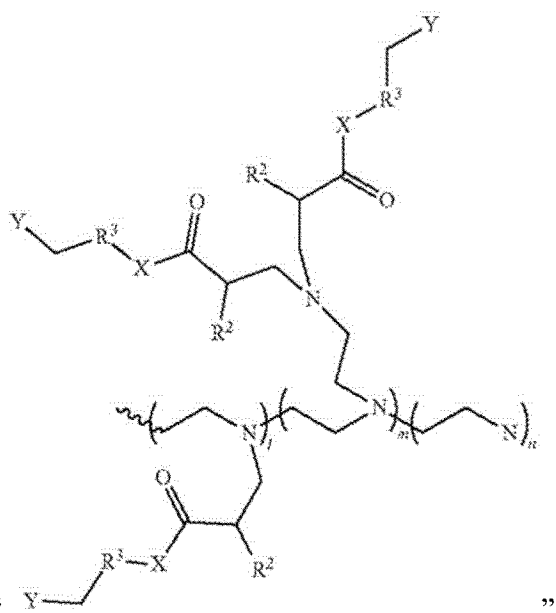"

CERTIFICATE OF CORRECTION (continued)
U.S. Pat. No. 11,685,709 B2

In Column 56, Claim 1, Lines 1-20:

DELETE: "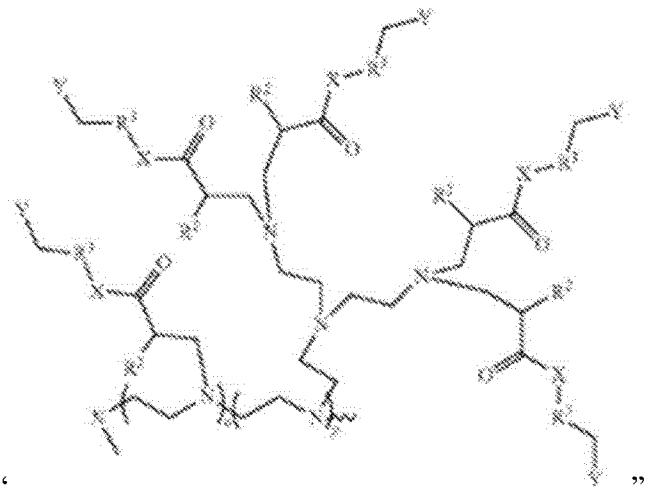"

INSERT: --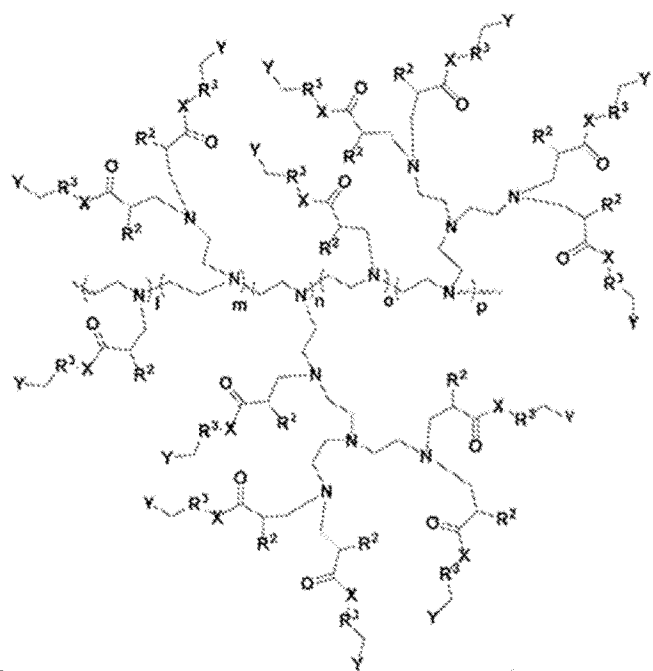--

CERTIFICATE OF CORRECTION (continued)
U.S. Pat. No. 11,685,709 B2

In Column 56, Claim 1, Lines 23-43:

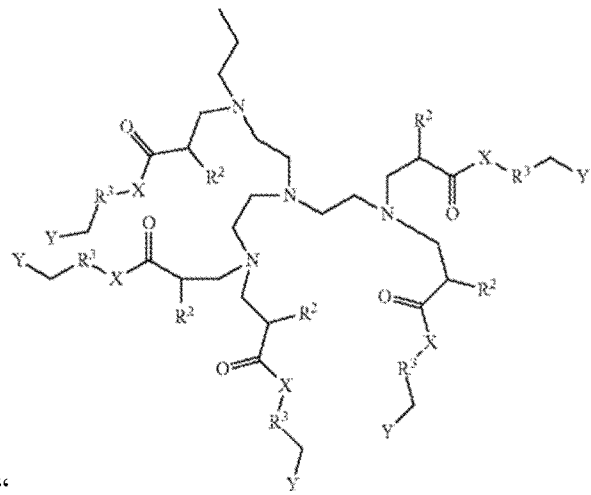

DELETE: " "

In Column 56, Claim 1, Line 57:
DELETE: "$R_5$"
INSERT: --$R^5$--

In Columns 57-58, Claim 11, Line 39:

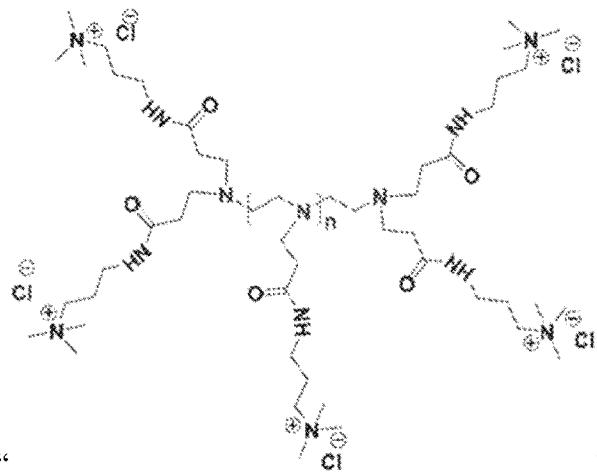

DELETE: " "